(12) United States Patent
Roman

(10) Patent No.: US 11,147,320 B2
(45) Date of Patent: **\*Oct. 19, 2021**

(54) SUPPORT FOR BODY PORTION

(71) Applicant: EZBRA ADVANCED WOUND CARE LTD., Tel-Aviv (IL)

(72) Inventor: Efrat Roman, Tel-Aviv (IL)

(73) Assignee: EZBRA ADVANCED WOUND CARE LTD., Tel-Aviv (IL)

( \* ) Notice: Subject to any disclaimer, the term of this patent is extended or adjusted under 35 U.S.C. 154(b) by 701 days.

This patent is subject to a terminal disclaimer.

(21) Appl. No.: 15/511,423

(22) PCT Filed: Feb. 17, 2016

(86) PCT No.: PCT/IL2016/050188
§ 371 (c)(1),
(2) Date: Mar. 15, 2017

(87) PCT Pub. No.: WO2016/132360
PCT Pub. Date: Aug. 25, 2016

(65) Prior Publication Data
US 2017/0245557 A1   Aug. 31, 2017

(30) Foreign Application Priority Data
Feb. 17, 2015   (IL) .......................................... 237289

(51) Int. Cl.
*A41C 3/00*   (2006.01)
*A41C 3/02*   (2006.01)
(Continued)

(52) U.S. Cl.
CPC .............. *A41C 3/0064* (2013.01); *A41C 3/02* (2013.01); *A41C 3/06* (2013.01); *A61F 5/03* (2013.01);
(Continued)

(58) Field of Classification Search
CPC ........... A41C 3/06; A41C 3/02; A41C 3/0064; A61F 5/03; A61F 13/145; A61F 13/14; A61F 13/143
See application file for complete search history.

(56) References Cited

U.S. PATENT DOCUMENTS 1,448,639 A   3/1923 Reece
1,702,922 A   2/1929 Yerkes
(Continued)

FOREIGN PATENT DOCUMENTS

DE   297 06 690 U1   6/1997
DE   10 2006 017 567 A1   10/2007
(Continued)

OTHER PUBLICATIONS

Compression Bra & Belt (Model 519)—Dianne's Mastectomy, two pages, retrieved from online on Jul. 9, 2015, http://diannesmasectomy.com/accessories/compression-bra-belt-model-519/.
(Continued)

*Primary Examiner* — Khoa D Huynh
*Assistant Examiner* — Brieanna Szafran
(74) *Attorney, Agent, or Firm* — Vorys, Sater, Seymour and Pease LLP; William L. Klima

(57) ABSTRACT

A variety of body supports are disclosed for supporting a body portion, for example, for supporting a chest in a donned configuration. In some examples, the body support includes a first support panel having one or more first tongues projecting outwardly therefrom, a second support panel having one or more second tongues projecting outwardly therefrom, a connecting section, joining the first support panel to said second support panel in longitudinal spaced relationship along an imaginary longitudinal midline of the body support, the first tongue and the second tongue being on opposite transverse sides of a mid-line of
(Continued)

the body support, a first fastener and a second fastener. The body support may further include a doffed configuration in which the first support panel and the second support panel are non-contiguous with respect to one another.

27 Claims, 17 Drawing Sheets

(51) Int. Cl.
  *A41C 3/06* (2006.01)
  *A61F 13/14* (2006.01)
  *A61F 5/03* (2006.01)
(52) U.S. Cl.
  CPC ........ *A61F 13/145* (2013.01); *A41B 2400/52* (2013.01)

(56) References Cited

U.S. PATENT DOCUMENTS

| | | |
|---|---|---|
| 2,412,075 A | 12/1946 | Boone |
| 2,427,402 A | 9/1947 | Gluckin |
| 2,662,522 A | 12/1953 | Muller |
| 2,970,597 A | 2/1961 | Michel |
| 3,598,114 A | 8/1971 | Lewis |
| 3,651,522 A | 3/1972 | Bernfeld |
| 4,257,412 A | 3/1981 | Guttentag |
| 4,297,997 A | 11/1981 | Clayton |
| 4,530,361 A | 7/1985 | Wooten |
| 5,032,104 A | 7/1991 | Rainville |
| 5,098,331 A | 3/1992 | Corrado |
| 5,152,741 A | 10/1992 | Farnio |
| 5,538,502 A | 7/1996 | Johnstone |
| 5,868,601 A | 2/1999 | Kelemencky |
| 6,068,538 A | 5/2000 | Alleyne |
| RE36,869 E | 9/2000 | Ewen |
| 6,220,924 B1 | 4/2001 | Kobayashi et al. |
| 6,319,091 B1 | 11/2001 | Kilbride et al. |
| D475,506 S | 6/2003 | Hoffman et al. |
| D475,835 S | 6/2003 | Hoffman et al. |
| 7,909,675 B1 | 3/2011 | Rainey |
| 9,398,973 B1 | 7/2016 | Goodson |
| 9,681,692 B2 | 6/2017 | Hansen |
| 2005/0014451 A1 | 1/2005 | Wicks |
| 2006/0228988 A1 | 10/2006 | Weyenberg et al. |
| 2010/0081359 A1 | 4/2010 | Cavosie |
| 2013/0115852 A1 | 5/2013 | Blackwell |
| 2013/0333706 A1 | 12/2013 | Bauerfeind |
| 2014/0378933 A1 | 12/2014 | Lucas et al. |
| 2015/0099420 A1 | 4/2015 | Reinhard |

FOREIGN PATENT DOCUMENTS

| | | | |
|---|---|---|---|
| EP | 3108863 A1 * | 12/2016 | ............ A61F 5/03 |
| FR | 2 252 061 A1 | 6/1975 | |
| WO | 2007/118580 A1 | 10/2007 | |
| WO | 2008/017707 A1 | 2/2008 | |

OTHER PUBLICATIONS

Post-Op Bra :: Sports Supports—Mobility—Heathcare Products, two pages, retrieved from online on Jul. 9, 2015, http://www.healthandcare.co.uk/post-breast-surgery-range/post-op-bra.html.

* cited by examiner

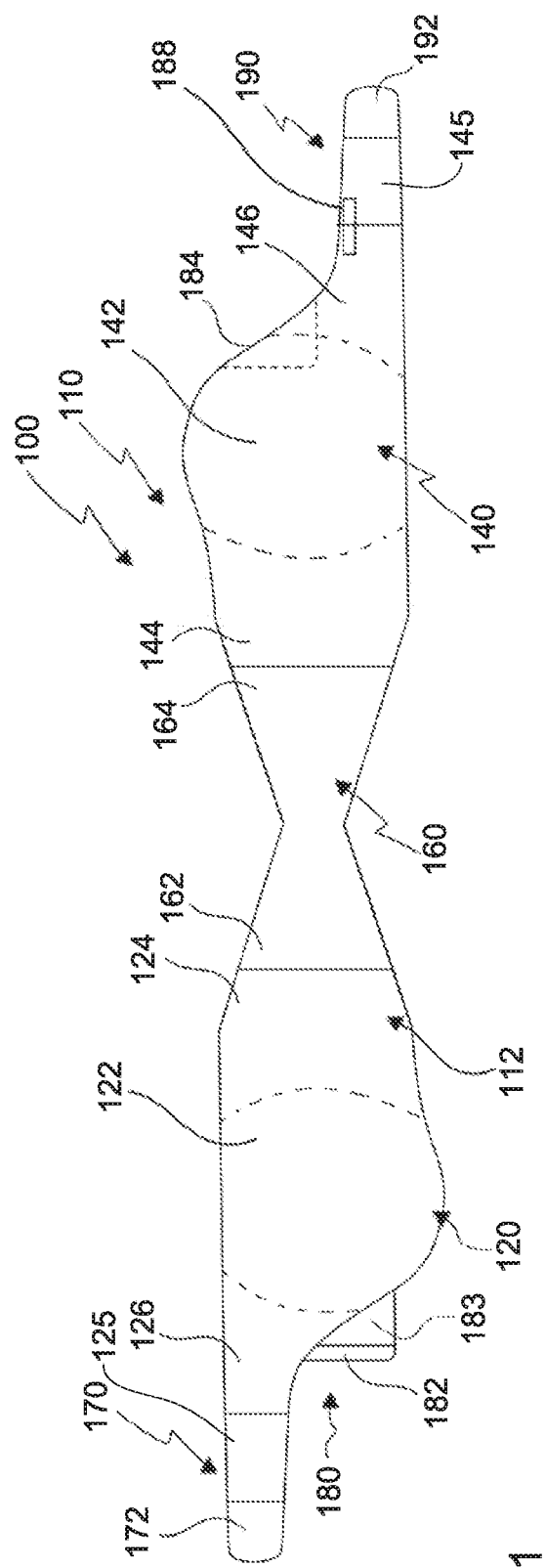
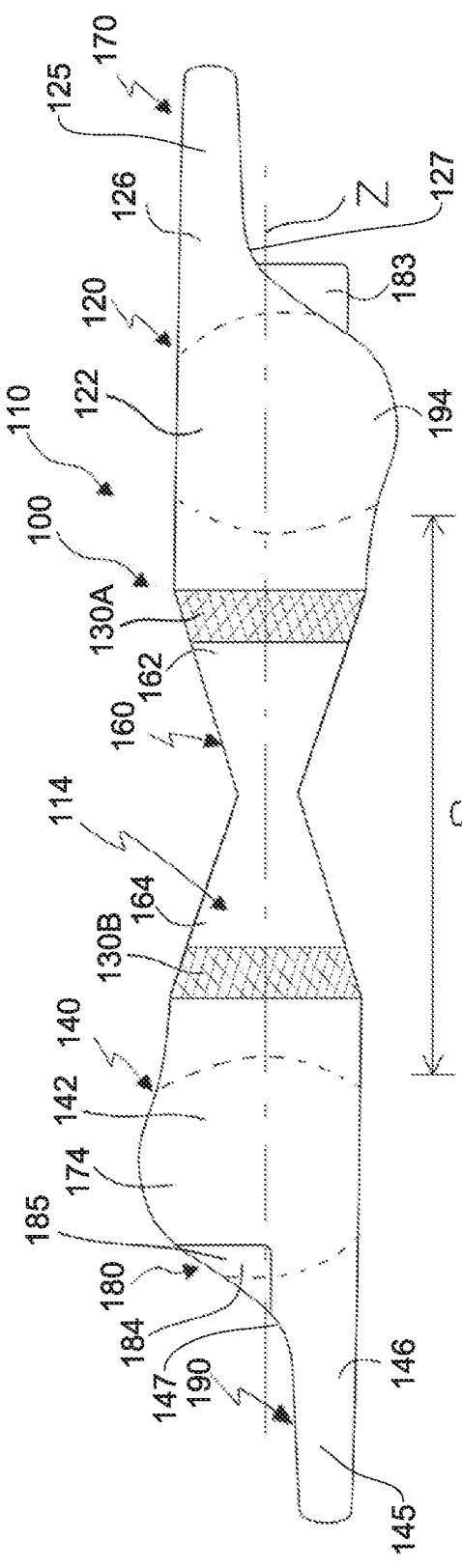
Fig. 1
Fig. 2

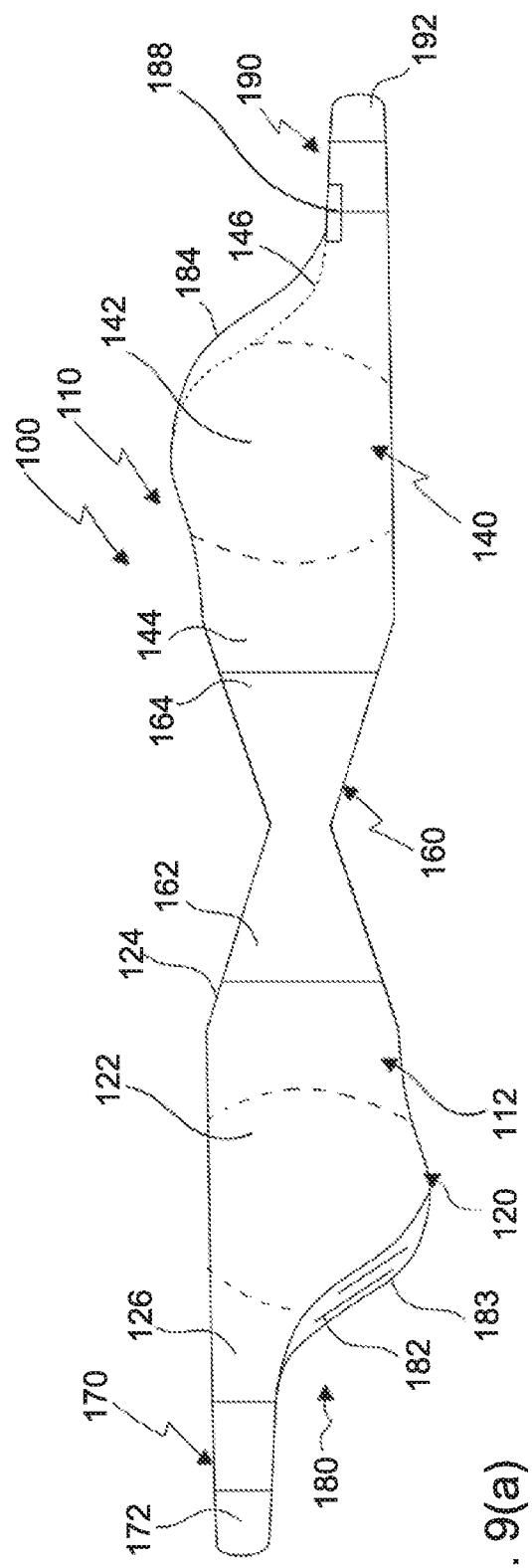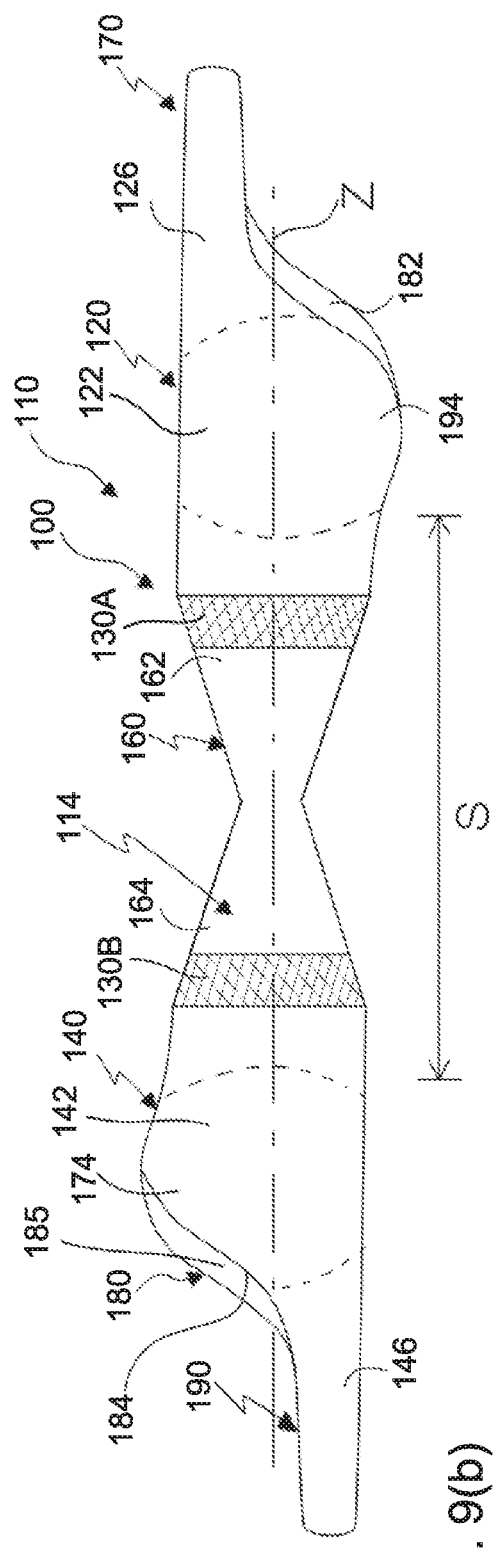
Fig. 9(a)
Fig. 9(b)

SUPPORT FOR BODY PORTION

TECHNOLOGICAL FIELD

The presently disclosed subject matter relates to supports for body portions, in particular chest supports, for example for providing support for the breast areas of the chest.

BACKGROUND

Supports for body portions are known, for example bandages.

Some such supports are configured for the chest, and in particular for providing support for the breast areas of the chest, and can include some varieties of chest garments. These may be used for post-surgical breast dressing and/or for applying pressure onto the chest after surgery, and/or for stabilizing the breast, e.g. after breast implant. Such chest garments are typically designed the surround the wearer's mid to upper torso and support the chest.

Some chest garments for use after cosmetic or surgical breast surgery, and/or other chest garments are disclosed in US Patent Publication Nos. 1,448,639; 2,427,402; 2,662,522; 2,970,597; 3,651,522; 4,257,412; 4,530,361; 5,098,331; 5,152,741; 5,538,502; 5,868,601; 6,220,924; 6,319,091; 7,909,675; in US Patent Application Publication No. 2013/115852; in US design patent No. D475506S; in International Patent Application Publication Nos. 2007/118580 and 2008/017707; in German Patent Application publication No. 29706690; and in French Patent Application Publication No. 2 252 061.

In addition, compression bras may be found on line for example at http://diannesmastectomy.com/accessories/compression-bra-belt-model-519/; and at http://www.healthandcare.co.uk/post-breast-surgery-range/post-op-bra.html

EMBODIMENTS

Some non-limiting embodiments encompassed by the present disclosure are defined in the following numbered clauses:

1. A body support for covering and supporting at least a first body area and a second body area of a body portion, each one of the first body area and the second body area being on a different lateral side of a median plane of the body portion, the body support having a donned configuration and a doffed configuration with respect to the body portion, the body support comprising:
   a first support comprising a resilient first panel, a first inner lateral end and a free first outer lateral end, spaced from said first inner lateral end;
   a second support comprising a resilient second panel, a second inner lateral end and a free second outer lateral end, spaced from said first inner lateral end;
   a connecting section joined to the first inner lateral end and to the second inner lateral end for thereby enabling, in the donned configuration, encircling and supporting the body portion when affixed thereto;
   at least one first tongue outwardly projecting from said first outer lateral end and comprising a first fastener configured for selectively and reversibly affixing said first support with respect to said second support at least at one first location, in the donned configuration, such that a portion of said first tongue is in overlapping abutting relationship with a respective portion of said second support, wherein to enable a first support pressure to be induced to the first body area by abutting contact therewith; and
   at least one second tongue outwardly projecting from said second outer lateral end and comprising a second fastener, different from said first fastener, configured for selectively and reversibly affixing said second support with respect to said first support at least at one second location, in the donned configuration, such that a portion of said second tongue is in overlapping abutting relationship with a respective portion of said first support, wherein to enable a second support pressure to be induced to the second body area by abutting contact therewith;
   wherein in the doffed configuration the first support and the second support are non-contiguous with respect to one another.
2. The body support according to clause 1, wherein at said at least one first location, a portion of said first outer lateral end is in overlapping abutting relationship with a respective portion of said second support.
3. The body support according to clause 1 or 2, wherein said first support pressure is induced to the first body area by applying a first tension to said first outer lateral end.
4. The body support according to clause 3, wherein said first tension is applied by laterally pulling the first outer lateral end over the second support.
5. The body support according to any one of clauses 1 to 4, comprising a plurality of said first locations, each having a different lateral spacing with respect to the second support, wherein affixing said first support with respect to said second support at each different said first locations enables the first support pressure to be correspondingly varied.
6. The body support according to any one of clauses 1 to 5, wherein said first fastener is configured for reversibly affixing said at least one first tongue with respect to an outer facing side of the second support.
7. The body support according to any one of clauses 1 to 6, wherein said first outer lateral end comprises a plurality of said first tongues, each said first tongue outwardly projecting from said first panel, and wherein said first fastener is configured for reversibly affixing each respective said at least one first tongue with respect to an outer facing side of the second support.
8. The body support according to any one of clauses 1 to 7, wherein said second outer lateral end comprises at least one first opening allowing a respective said first tongue to be looped therethrough and in overlapping relationship with the first panel, and wherein said second fastener is configured for reversibly affixing the respective said first tongue with respect to an outer facing side of the first support.
9. The body support according to any one of clauses 1 to 8, wherein at said at least one second location, a portion of said second outer lateral end is in overlapping abutting relationship with a respective portion of said first support.
10. The body support according to any one of clauses 1 to 9, wherein said second support pressure is induced to the second body area by applying a second tension to said second outer lateral end.
11. The body support according to clause 10, wherein said second tension is applied by laterally pulling the second outer lateral end over the first support.
12. The body support according to any one of clauses 1 to 11, comprising a plurality of said second locations, each having a different lateral spacing with respect to the first support, wherein affixing said second support with respect to said first support at each different said second locations enables the first support pressure to be correspondingly varied.

13. The body support according to any one of clauses 1 to 12, wherein said second fastener is configured for reversibly affixing said at least one second tongue with respect to an outer facing side of the first support.

14. The body support according to any one of clauses 1 to 13, wherein said second outer lateral end comprises a plurality of said second tongues, each said second tongue outwardly projecting from said second panel, and wherein said second fastener is configured for reversibly affixing said at least one second tongue with respect to an outer facing side of the first support.

15. The body support according to any one of clauses 1 to 14, wherein said first outer lateral end comprises at least one second opening allowing a respective said second tongue to be looped therethrough and in overlapping relationship with the second panel, and wherein said first fastener is configured for reversibly affixing the respective said second tongue with respect to an outer facing side of the second support.

16. The body support according to any one of clauses 10 to 15, wherein said first tension is applied laterally at a relatively superior position and said second tension is applied laterally at a relatively inferior position.

17. The body support according to any one of clauses 10 to 15, wherein said first tension is applied laterally at a relatively inferior position and said second tension is applied laterally at a relatively superior position.

18. The body support according to any one of clauses 1 to 17, wherein the connecting section is laterally joined to each one of the first inner lateral end and to the second inner lateral end.

19. The body support according to any one of clauses 1 to 18, wherein said connecting section is joined to the first inner lateral end and to the second inner lateral end for thereby enabling encircling and supporting the body portion when affixed thereto in the donned configuration, such that said first panel is in overlying abutting relationship with the first body area and said second panel is in overlying abutting relationship with the second body area, and such that at least a portion of said connecting section is in overlying abutting relationship with a back of the body portion.

20. The body support according to any one of clauses 1 to 19, further comprising at least one auxiliary fastener, different from said first fastener and said second fastener, each said at least one auxiliary fastener configured for reversibly affixing together the first support and the second support at an anterior position with respect to the body portion.

21. The body support according to clause 20, wherein at least one said auxiliary fastener is configured for reversibly affixing together the first support and the second support at a generally medial anterior position, generally corresponding to a median plane of the body portion.

22. The body support according to any one of clauses 1 to 21, further comprising a pair of stabilizing panels, positioned on the body support a first said stabilizing panel overlying a first part of the first support and a first part of the connecting section, and a second said stabilizing panel overlying a second part of the second support and a second part of the connecting section, wherein each said stabilizing panels is generally non-elastic, at least in a lateral direction.

23. The body support according to any one of clauses 1 to 22, wherein:
said connecting section joins said first support to said second support in longitudinal spaced relationship along an imaginary longitudinal mid-line of the body support;
said at least one first tongue is transversely spaced from said mid-line on a first transverse side of said mid-line, and said at least one second tongue is transversely spaced from said mid-line on a second transverse side of said mid-line, wherein said first transverse side and said second transverse side are opposite transverse sides of the mid-line.

24. The body support according to any one of clauses 1 to 23, wherein the first support further comprises at least one first auxiliary tongue projecting from said first outer lateral end and comprising a first auxiliary fastener configured for selectively and reversibly affixing a respective said first auxiliary tongue with respect to said first support at least at one first location, in the donned configuration, such that a portion of said first auxiliary tongue is in overlapping abutting relationship with a respective portion of said first support, wherein to enhance said first support pressure.

25. The body support according to clause 24, wherein each said first auxiliary tongue is connected at one end thereof to an inner end of a corresponding said first tongue, wherein at least prior to donning the body support said first auxiliary tongue is in overlying relationship with the corresponding said first tongue, and wherein said first auxiliary tongue is pivoted about said one end thereof away from the corresponding said first tongue to enable said first auxiliary tongue to be affixed with respect to said first support.

26. The body support according to any one of clauses 1 to 25, wherein the second support further comprises at least one second auxiliary tongue projecting from said second outer lateral end and comprising a second auxiliary fastener configured for selectively and reversibly affixing a respective said second auxiliary tongue with respect to said second support at least at one second location, in the donned configuration, such that a portion of said second auxiliary tongue is in overlapping abutting relationship with a respective portion of said second support, wherein to enhance said second support pressure.

27. The body support according to clause 26, wherein each said second auxiliary tongue is connected at one end thereof to an inner end of a corresponding said second tongue, wherein at least prior to donning the body support said second auxiliary tongue is in overlying relationship with the corresponding said second tongue, and wherein said second auxiliary tongue is pivoted about said one end thereof away from the corresponding said second tongue to enable said second auxiliary tongue to be affixed with respect to said second support.

28. The body support according to any one of clauses 1 to 27, wherein in the doffed configuration the first support and the second support are permanently joined to one another exclusively via said connecting section.

29. The body support according to any one of clauses 1 to 28, wherein at least in doffed configuration said free first outer lateral end and said free second outer lateral end are unattached to one another.

30. The body support according to any one of clauses 1 to 29, wherein at least in the doffed configuration said first support and said second support are unattached directly to one another.

31. The body support according to any one of clauses 1 to 30, wherein in use of the body support when supporting the body portion, there is an absence of a permanent fixation between said free first outer lateral end and said free second outer lateral end.
32. The body support according to any one of clauses 1 to 31, wherein in the donned configuration the body support is affixed to the body portion exclusively via said first pressure and said second pressure.
33. The body support according to any one of clauses 1 to 32, wherein first support pressure results in a tightening of the body support over the body portion, at the general location of the at least one first tongue, in a predominantly lateral direction with respect to the body portion.
34. The body support according to any one of clauses 1 to 33, wherein second support pressure results in a tightening of the body support over the body portion, at the general location of the at least one second tongue, in a predominantly lateral direction with respect to the body portion.
35. The body support according to any one of clauses 1 to 34, wherein said at least one first tongue is in parallel transversely spaced relationship with respect to said at least one second tongue.
36. The body support according to any one of clauses 1 to 35, wherein in the donned configuration, a first edge of first outer lateral end is in abutment with a second edge of said second outer lateral end.
37. The body support according to any one of clauses 1 to 35, wherein in the donned configuration, a first edge of first outer lateral end is in abutment with a second edge of said second outer lateral end at an abutment zone in cross-over configuration, to allow a first portion of said first outer lateral end to overlie a second portion of said second outer lateral end, while concurrently allowing a first portion of said second outer lateral end to overlie a second portion of said first outer lateral end.
38. The body support according to any one of clauses 1 to 37, wherein the body support is formed as a disposable article.
39. The body support according to any one of clauses 1 to 37, wherein the body support is formed as a multiple use article.
40. The body support according to any one of clauses 1 to 39, wherein the first fastener and the second fastener are configured for applying said first support pressure and said second support pressure, respectively, independently of one another.
41. The body support according to any one of clauses 1 to 40, wherein the first fastener and the second fastener are configured for applying said first support pressure different from said second support pressure.
42. The body support according to any one of clauses 1 to 41, particularly configured as chest support, wherein:
said body portion is a torso, said first body area is a first breast area and said second body area is a second breast area of a chest corresponding to the torso, each one of the first breast area and the second breast area being on a different lateral side of the midsagittal plane of the torso;
said first panel is a first breast receiving panel, and said second panel is a second breast receiving panel.
43. The body support according to clause 42, wherein said at least one first tongue is transversely spaced with respect to said at least one second tongue by a transverse spacing, wherein said transverse spacing is generally not less than a height dimension of the breast areas.
44. The body support according to any one of clauses 42 to 43, comprising a pair of stabilizing panels, positioned on the body support such as to be in overlying relationship with a respective one of the left side of an upper rib cage and the right side the upper rib cage, respectively, of the torso, when the body support is encircling the torso and supporting the chest in the donned configuration, wherein each said stabilizing panels is generally non-elastic, at least in a lateral direction.
45. The body support according to any one of clauses 1 to 41, wherein said body portion is any one of an arm, a palm, a finger, a leg, a foot, a toe, an abdomen, a hip, a neck, each representing a separate and independent embodiment of the present disclosure.
46. A method of donning a body support on a body portion, comprising:
(a) providing the body support as defined in any one of clauses 42 to 44;
(b) encircling the torso with the body support such that first breast receiving panel is in overlying abutting relationship with the first breast area, the second breast receiving panel is in overlying abutting relationship with the second breast area, and the connecting is in overlying abutting relationship with a back of the torso;
(c) applying said first tension to the first breast receiving panel via the first lateral outer end, and affixing the first breast receiving panel with respect to the second support at a corresponding said first position while maintaining said first tension, such as to induce said first support pressure to said first breast area;
(d) applying said second tension to the second breast receiving panel via the second lateral outer end, and affixing the second breast receiving panel with respect to the first support at a corresponding said second position while maintaining said second tension, such as to induce said second support pressure to said second breast area.
47. A body support for selectively encircling a body part in abutment therewith and supporting at least a first body area and a second body area thereof in a donned configuration, each one of the first body area and the second body area being on a different lateral side of a median plane of the body part, the body support further having a doffed configuration with respect to the body portion, the body support comprising:
a resilient first support panel for abutting the first body area;
a resilient second support panel for abutting the second body area;
a flexible connecting section, joining said first support panel to said second support panel in longitudinal spaced relationship along an imaginary longitudinal mid-line of the body support;
at least one flexible first tongue projecting outwardly from the first support panel in a general first longitudinal direction away from the connecting section, each said first tongue being transversely spaced from said mid-line on a first transverse side of said mid-line;
at least one flexible second tongue projecting outwardly from the second breast support panel in a general second longitudinal direction away from the connecting section, each said second tongue being transversely spaced from said mid-line on a second transverse side of said mid-line;
said first transverse side and said second transverse side being opposite transverse sides of the mid-line;

a first fastener operative for selectively and reversibly affixing each said first tongue to said second support panel at least at one first relative spatial disposition on said first transverse side of the mid-line;

a second fastener operative for selectively and reversibly affixing each said second tongue to said first support panel at least at one second relative spatial disposition on said second transverse side of the mid-line;

wherein in the doffed configuration the first support panel and the second support panel are non-contiguous with respect to one another.

48. The body support according to clause 47, wherein said longitudinal spaced relationship is such that, in said donned configuration, said first support panel is in overlying abutting relationship with the first body area and said second support panel is in overlying abutting relationship with the second body area.

49. The body support according to any one of clauses 47 to 48, further comprising at least one auxiliary fastener, different from said first fastener and said second fastener, each said at least one auxiliary fastener configured for reversibly affixing together the first support panel and the second support panel in the donned configuration.

50. The body support according to clause 49, wherein at least one said auxiliary fastener is configured for reversibly affixing together the first support panel and the second support panel at a generally medial anterior position.

51. The body support according to any one of clauses 47 to 50, further comprising a pair of stabilizing panels, positioned on the body support, a first said stabilizing panel overlying a first part of the first support panel and a first part of the connecting section, and a second said stabilizing panel overlying a second part of the second support panel and a second part of the connecting section, wherein each said stabilizing panels is generally non-elastic, at least in a lateral direction.

52. The body support according to any one of clauses 47 to 51, wherein said first support panel comprises a plurality of said first tongues, each said first tongue outwardly projecting from said first support panel, and wherein said first fastener is configured for reversibly affixing each respective said at least one first tongue with respect to an outer facing side of the second support panel.

53. The body support according to any one of clauses 47 to 52, wherein said second support panel comprises at least one first opening allowing a respective said first tongue to be looped therethrough and in overlapping relationship with the first support panel, and wherein said second fastener is configured for reversibly affixing the respective said first tongue with respect to an outer facing side of the first support panel.

54. The body support according to any one of clauses 47 to 53, wherein said second support panel comprises a plurality of said second tongues, each said second tongue outwardly projecting from said second support panel, and wherein said second fastener is configured for reversibly affixing said at least one second tongue with respect to an outer facing side of the first support panel.

55. The body support according to any one of clauses 47 to 54, wherein said first support panel comprises at least one second opening allowing a respective said second tongue to be looped therethrough and in overlapping relationship with the second support panel, and wherein said first fastener is configured for reversibly affixing the respective said second tongue with respect to an outer facing side of the second support panel.

56. The body support according to any one of clauses 47 to 55, configured for enabling encircling and supporting the body portion when affixed thereto in the donned configuration, such that said first support panel is in overlying abutting relationship with the first body area and said second support panel is in overlying abutting relationship with the second body area, and such that at least a portion of said connecting section is in overlying abutting relationship with a back of the body portion.

57. The body support according to any one of clauses 47 to 56, further comprising at least one auxiliary fastener, different from said first fastener and said second fastener, each said at least one auxiliary fastener configured for reversibly affixing together the first support panel and the second support panel at an anterior position with respect to the body portion.

58. The body support according to clause 57, wherein at least one said auxiliary fastener is configured for reversibly affixing together the first support panel and the second support panel at a generally medial anterior position, generally corresponding to a median plane of the body portion.

59. The body support according to any one of clauses 47 to 58, wherein the first support panel further comprises at least one first auxiliary tongue projecting from said first support panel and comprising a first auxiliary fastener configured for selectively and reversibly affixing a respective said first auxiliary tongue with respect to said first support panel at least at one first location, in the donned configuration, such that a portion of said first auxiliary tongue is in overlapping abutting relationship with a respective portion of said first support panel.

60. The body support according to clause 59, wherein each said first auxiliary tongue is connected at one end thereof to an inner end of a corresponding said first tongue, wherein at least prior to donning the body support said first auxiliary tongue is in overlying relationship with the corresponding said first tongue, and wherein said first auxiliary tongue is pivoted about said one end thereof away from the corresponding said first tongue to enable said first auxiliary tongue to be affixed with respect to said first support panel.

61. The body support according to any one of clauses 47 to 60, wherein the second support panel further comprises at least one second auxiliary tongue projecting from said second support panel and comprising a second auxiliary fastener configured for selectively and reversibly affixing a respective said second auxiliary tongue with respect to said second support panel at least at one second location, in the donned configuration, such that a portion of said second auxiliary tongue is in overlapping abutting relationship with a respective portion of said second support panel.

62. The body support according to clause 61, wherein each said second auxiliary tongue, connected at one end thereof to an inner end of a corresponding said second tongue, wherein at least prior to donning the body support said second auxiliary tongue is in overlying relationship with the corresponding said second tongue, and wherein said second auxiliary tongue is pivoted about said one end thereof away from the corresponding said second tongue to enable said second auxiliary tongue to be affixed with respect to said second support panel.

63. The body support according to any one of clauses 47 to 62, wherein in the doffed configuration the first support panel and the second support panel are permanently joined to one another exclusively via said connecting section.

64. The body support according to any one of clauses 47 to 63, wherein at least doffed configuration said first support panel and said second support panel are unattached to one another.

65. The body support according to any one of clauses 47 to 64, wherein in use of the body support when supporting the body portion, there is an absence of a permanent direct fixation between said first support panel and said second support panel.

66. The body support according to any one of clauses 47 to 65, wherein in the donned configuration, said at least one first tongue is fixed to said second support panel, wherein to enable a first support pressure to be induced to the first body area by abutting contact therewith; and said at least one second tongue is fixed to said first support panel, wherein to enable a second support pressure to be induced to the second body area by abutting contact therewith.

67. The body support according to clause 66, wherein the donned configuration the body support is affixed to the body portion exclusively via said first pressure and said second pressure.

68. The body support according to any one of clauses 66 to 67, wherein first support pressure results in a tightening of the body support over the body portion, at the general location of the at least one first tongue, in a predominantly lateral direction with respect to the body portion.

69. The body support according to any one of clauses 66 to 68, wherein second support pressure results in a tightening of the body support over the body portion, at the general location of the at least one second tongue, in a predominantly lateral direction with respect to the body portion.

70. The body support according to any one of clauses 47 to 70, wherein said at least one first tongue is in parallel transversely spaced relationship with respect to said at least one second tongue.

71. The body support according to any one of clauses 47 to 70, particularly configured as chest support, wherein:
said body portion is a torso, said first body area is a first breast area and said second body area is a second breast area of a chest corresponding to the torso, each one of the first breast area and the second breast area being on a different lateral side of the midsagittal plane of the torso;
said first support panel is a first breast receiving panel, and said second support panel is a second breast receiving panel.

72. The body support according to clause 71, wherein said at least one first tongue is transversely spaced with respect to said at least one second tongue by a transverse spacing, wherein said transverse spacing is generally not less than a height dimension of the breast areas.

73. The body support according to any one of clauses 71 to 72, comprising a pair of stabilizing panels, positioned on the body support such as to be in overlying relationship with a respective one of the left side of an upper rib cage and the right side the upper rib cage, respectively, of the torso, when the body support is encircling the torso and supporting the chest in the donned configuration, wherein each said stabilizing panels is generally non-elastic, at least in a lateral direction.

74. The body support according to any one of clauses 47 to 70, wherein said body portion is any one of: an arm, a palm, a finger, a leg, a foot, a toe, an abdomen, a hip, a neck, each representing an independent and separate embodiment herein.

75. The body support according to any one of clauses 47 to 74, wherein said first tongue projects outwardly from the first support panel in a direction generally parallel to said mid-line.

76. The body support according to any one of clauses 47 to 75, wherein said second tongue projects outwardly from the second support panel in a direction generally parallel to said mid-line.

77. The body support according to any of clauses 47 to 76, wherein the body support is formed as a disposable article.

78. The body support according to any one of clauses 47 to 76, wherein the body support is formed as a multiple use article.

78. A method of donning a body support on a body portion, comprising:
(a) providing the body support as defined in any one of clauses 71 to 73;
(b) encircling the torso with the body support such that first breast receiving panel is in overlying abutting relationship with the first breast area, the second breast receiving panel is in overlying abutting relationship with the second breast area, and the connecting is in overlying abutting relationship with a back of the torso;
(c) applying said first tension to the first breast receiving panel via the first lateral outer end, and affixing the first breast receiving panel with respect to the second support at a corresponding said first position while maintaining said first tension, such as to induce said first support pressure to said first breast area;
(d) applying said second tension to the second breast receiving panel via the second lateral outer end, and affixing the second breast receiving panel with respect to the first support at a corresponding said second position while maintaining said second tension, such as to induce said second support pressure to said second breast area.

General Description

Herein "body portion" refers to a part of the body having an external facing surface and that can be encircled by a band, for example. Such body portions can include, for example, any one of the following: an arm, a palm, a finger, a leg, a foot, a toe, an abdomen, a hip, a neck. Herein "body" includes the human body, male or female, and can also include animal bodies, in particular of primates.

The presently disclosed subject matter provides, according to one of its aspects, a chest support for covering and supporting at least a first breast area and a second breast area of a chest, each one of the first breast area and the second breast area being on a different lateral side of the midsagittal plane of the corresponding torso, the chest support comprises:
a first breast support comprising a resilient first breast receiving panel, a first inner lateral end and a free first outer lateral end;
a second breast support comprising a resilient second breast receiving panel, a second inner lateral end and a free second outer lateral end;
a connecting section joined to the first inner lateral end and to the second inner lateral end for thereby enabling encircling and supporting the torso when affixed thereto;
a first fastener configured for selectively and reversibly affixing said first breast support with respect to said second breast support at least at one first location, such that a portion of said first breast support is in overlapping abutting relationship with a respective portion of said second breast support, wherein to enable a first support pressure to be induced to the first breast area by abutting contact therewith; and a second fastener, different from said first fastener, configured for selectively and reversibly affixing said second breast support with respect to said first breast support at least at one second location, such that a portion of said second breast support is in overlapping abutting relationship with a respective portion of said first breast support, wherein to enable a second support pressure to be induced to the second breast area by abutting contact therewith.

In particular, in the doffed configuration the first breast support and the second breast support are non-contiguous with respect to one another.

In an alternative example of the presently disclosed subject matter, there is provided a chest support for covering and supporting at least a first breast area and a second breast area of a chest, each one of the first breast area and the second breast area being on a different lateral side of the midsagittal plane of the corresponding torso, the chest support comprises:

a first breast support comprising a resilient first breast receiving panel, a first inner lateral end and a free first outer lateral end;

a second breast support comprising a resilient second breast receiving panel, a second inner lateral end and a free second outer lateral end;

a connecting section joined to the first inner lateral end and to the second inner lateral end for thereby enabling encircling and supporting the chest when affixed thereto;

a first fastener configured for selectively and reversibly affixing said first breast support with respect to said second breast support at least at one first location, wherein to enable a first support pressure to be, induced to the first breast area; and a second fastener, different from said first fastener, configured for selectively and reversibly affixing said second breast support with respect to said first breast support at least at one second location, wherein to enable a second support pressure to be induced to the second breast area;

wherein the first fastener and the second fastener are configured for applying said first support pressure and said second support pressure, respectively, independently of one another.

In yet another alternative example of the presently disclosed subject matter, there is provided a chest support for covering and supporting at least a first breast area and a second breast area of a chest, each one of the first breast area and the second breast area being on a different lateral side of the midsagittal plane of the corresponding torso, the chest support comprises:

a first breast support comprising a resilient first breast receiving panel, a first inner lateral end and a free first outer lateral end;

a second breast support comprising a resilient second breast receiving panel, a second inner lateral end and a free second outer lateral end;

a connecting section joined to the first inner lateral end and to the second inner lateral end for thereby enabling encircling and supporting the chest when affixed thereto;

a first fastener configured for selectively and reversibly affixing said first breast support with respect to said second breast support at least at one first location, wherein to enable a first support pressure to be induced to the first breast area; and a second fastener, different from said first fastener, configured for selectively and reversibly affixing said second breast support with respect to said first breast support at least at one second location, wherein to enable a second support pressure to be induced to the second breast area;

wherein the first fastener and the second fastener are configured for applying said first support pressure different from said second support pressure.

In yet a further alternative example of the presently disclosed subject matter, there is provided a chest support for covering and supporting at least a first breast area and a second breast area of a chest, each one of the first breast area and the second breast area being on a different lateral side of the midsagittal plane of the corresponding torso, the chest support comprises:

a first breast support comprising a resilient first breast receiving panel, a first inner lateral end and a free first outer lateral end;

a second breast support comprising a resilient second breast receiving panel, a second inner lateral end and a free second outer lateral end;

a connecting section joined to the first inner lateral end and to the second inner lateral end for thereby enabling encircling and supporting the chest when affixed thereto;

a first fastener configured for selectively and reversibly affixing said first breast support with respect to said second breast support at least at one first location, wherein to enable a first support pressure to be induced to the first breast area; and a second fastener, different from said first fastener, configured for selectively and reversibly affixing said second breast support with respect to said first breast support at least at one second location, wherein to enable a second support pressure to be induced to the second breast area;

wherein said first location is at a relative superior position and said second location is at a relative interior position.

In one preferred example, the presently disclosed subject flatter provides a chest support for selectively encircling a torso in abutment therewith and supporting at least a first breast area and a second breast area thereof, each one of the first breast area and the second breast area being on a different lateral side of the midsagittal plane of the torso, the chest support comprises:

a resilient first breast support panel for abutting the first breast area;

a resilient second breast support panel for abutting the second breast area;

a flexible connecting section, joining said first breast support panel to said second breast support panel in longitudinal spaced relationship along a mid-line of the chest support;

a flexible first tongue projecting outwardly from the first breast support panel in a general longitudinal direction away from the connecting section;

a flexible second tongue projecting outwardly from the second breast support panel in a general longitudinal direction away from the connecting section;

the first tongue and the second tongue being disposed in opposite sides of the mid-line;

a first fastener operative for selectively and reversibly affixing said first tongue to said second breast support panel at least at one first relative spatial disposition;

a second fastener operative for selectively and reversibly affixing said second tongue to said first breast support panel at least at one second relative spatial disposition.

When referring to a resilient material it is to be understood as encompassing any material that can be stretched and return to its original shape once the stretching force is removed. In other words, any material that is capable of recovering its original shape and size after removal of a strain applied thereon that causes deformation (e.g. springing back of fibers).

In accordance with some examples, one or more portions of the chest support is made of a resilient material.

Resilient material can be found in the textile industry, and can be composed of natural or synthetic substances. In some examples, the resilient material comprises synthetic material such as, without being limited thereto, polyurethane, polyester, rubber (e.g. synthetic rubber) and nylon.

When referring to flexible material it is be understood as encompassing any material that can be bended, folded, rolled, cramped and the like, without breaking. It is to be understood that in the context of the presently disclosed subject matter portions of the chest support are flexible; preferably the majority of the support is flexible, allowing it's circling around a subject's torso.

In some examples, portions of the chest support are flexible and resilient (elastic) and some other portions are only flexible, with no or only minimal elasticity.

In some examples, the chest support is such that at the at least one first location, a portion of the first outer lateral end is in overlapping abutting relationship with a respective portion of said second breast support.

In some examples, the first support pressure is induced to the first breast area by applying a first tension to the first outer lateral end. In some examples, the first tension is applied by laterally pulling the first outer lateral end over the second breast support.

In some examples, the chest support comprises a plurality of said first locations, each having a different lateral spacing with respect to the second breast support, wherein affixing said first breast support with respect to said second breast support at each different said first locations enables the first support pressure to be correspondingly varied.

In some examples, the first outer lateral end comprises at least one first tongue laterally projecting from said first breast receiving panel, and the first fastener is configured for reversibly affixing the at least one first tongue with respect to an outer facing side of the second breast support.

In some examples, the first outer lateral end comprises a plurality of first tongues, each laterally projecting from the first breast receiving panel, and the first fastener is configured for reversibly affixing the at least one first tongue with respect to an outer facing side of the second breast support.

In some examples, the first breast support comprises at least one first tongue laterally projecting from said first breast receiving panel, and wherein said second outer lateral end comprises at least one first opening allowing a respective said first tongue to be looped therethrough and in overlapping relationship with the first breast receiving panel, and wherein said second fastener is configured for reversibly affixing the respective said first tongue with respect to an outer facing side of the first breast support.

In yet some examples, the first breast support comprises at least one first tongue laterally projecting from the first breast receiving panel, and the second outer lateral end comprises at least one first opening allowing a respective said first tongue to be looped therethrough and in overlapping relationship with the first breast receiving panel, and yet the second fastener is configured for reversibly affixing the respective said first tongue with respect to an outer facing side of the first breast support.

In yet some additional examples, at the at least one second location, a portion of the second outer lateral end is in overlapping abutting relationship with a respective portion of said first breast support.

In some examples, the second support pressure is induced to the second breast area by applying a second tension to said second outer lateral end.

In some examples, the second tension is applied by laterally pulling the second outer lateral end over the first breast support.

In some examples, the chest support comprises a plurality of said second locations, each having a different lateral spacing with respect to the first breast support, wherein affixing said second breast support with respect to said first breast support at each different said second locations enables the first support pressure to be correspondingly varied.

In some examples, the second outer lateral end comprises at least one second tongue laterally projecting from said second breast receiving panel, and wherein said second fastener is configured for reversibly affixing said at least one second tongue with respect to an outer facing side of the first breast support.

In some examples, the second outer lateral end comprises a plurality of second tongues, each laterally projecting from said second breast receiving panel, and wherein said second fastener is configured for reversibly affixing said at least one second tongue with respect to an outer facing side of the first breast support.

In some examples, the second breast support comprises at least one second tongue laterally projecting from said second breast receiving panel, and wherein said first outer lateral end comprises at least one second opening allowing a respective said second tongue to be looped therethrough and in overlapping relationship with the second breast receiving panel, and wherein said first fastener is configured for reversibly affixing the respective said second tongue with respect to an outer facing side of the second breast support.

In one example, the first tension is applied laterally at a relatively superior position and the second tension is applied laterally at a relatively inferior position.

In an alternative example, the first tension is applied laterally at a relatively inferior position and the second tension is applied laterally at a relatively superior position.

In some examples, the connecting section is laterally joined to each one of the first inner lateral end and to the second inner lateral end. The connecting section can be, in some examples, joined to the first inner lateral end and to the second inner lateral end for thereby enabling encircling and supporting the chest when affixed thereto such that the first breast receiving panel is in overlying abutting relationship with the first breast area and the second breast receiving panel is in overlying abutting relationship with the second breast area, and such that at least a portion of the connecting section is in overlying abutting relationship with a back of the torso.

The chest support can also comprise at least one auxiliary fastener, different from the first fastener and the second fastener, each of the at least one auxiliary fastener configured for reversibly affixing together the first breast support and the second breast support at an anterior position with respect to the chest. In some examples, the at least one auxiliary fastener is configured for reversibly affixing together the first breast support and the second breast support at a generally medial anterior position, generally corresponding to the midsagittal plane.

The fasteners, the first, second, auxiliary or any other fastener used in the chest support can be of any type known in the art, such as in the textile industry or the like. In some examples, the fasteners, which can be the same or different within the chest support, comprises at least one garment fastener or bandage fastener. For example, and without being limited thereto, the fastener can be selected from the group consisting of hook-and-loop type fastener: button and hole fasteners; snap fasteners; hook and eye fasteners; belt buckle type fasteners; string fasteners; independent fasteners.

In some examples, the first fastener and the second fastener are configured for applying said first support pressure and said second support pressure, respectively, independently of one another.

In some examples, the first fastener and the second fastener are configured for applying said first support pressure different from said second support pressure.

The chest support can be formed as a disposable article, e.g. from disposable material as known, for example, in the textile and/or polymer and/or plastic industry and it can as well as be in the form or from materials suitable for multiple use.

The chest support comprises, in some examples, a pair of stabilizing panels, positioned on the chest support such as to be in overlying relationship with a respective one of the left side of the upper rib cage and the right side the upper rib cage, respectively, of the torso, when the chest support is encircling the torso and supporting the chest, wherein each said stabilizing panels is generally non-elastic at least in a lateral direction.

The present disclosure also provides a method of donning a chest support on a torso, the method comprises:
  (a) providing the chest support as disclosed herein;
  (b) encircling the torso with the chest support such that first breast receiving panel is in overlying abutting relationship with the first breast area, the second breast receiving panel is in overlying abutting relationship with the second breast area, and the connecting is in overlying abutting relationship with a back of the torso;
  (c) applying said first tension to the first breast receiving panel via the first lateral outer end, and affixing the first breast receiving panel with respect to the second breast support at a corresponding said first position while maintaining said first tension, such as to induce said first support pressure to said first breast area;
  (d) applying said second tension to the second breast receiving panel via the second lateral outer end, and affixing the second breast receiving panel with respect to the first breast support at a corresponding said second position while maintaining said second tension, such as to induce said second support pressure to said second breast area.

In some examples, the chest support (in particular the first breast support) further comprises at least one first auxiliary tongue projecting from said first outer lateral end and comprising a first auxiliary fastener configured for selectively and reversibly affixing a respective said first auxiliary tongue with respect to said first support at least at one first location, in the donned configuration, such that a portion of said first auxiliary tongue is in overlapping abutting relationship with a respective portion of said first support, wherein to enhance said first support pressure. For example, each said first auxiliary tongue is connected at one end thereof to an inner end of a corresponding said first tongue, wherein at least prior to donning the body support said first auxiliary tongue is in overlying relationship with the corresponding said first tongue, and wherein said first auxiliary tongue is pivoted about said one end thereof away from the corresponding said first tongue to enable said first auxiliary tongue to be affixed with respect to said first support.

In some examples, the chest support (in particular the second breast support) additionally or alternatively further comprises at least one second auxiliary tongue projecting from said second outer lateral end and comprising a second auxiliary fastener configured for selectively and reversibly affixing a respective said second auxiliary tongue with respect to said second support at least at one second location, in the donned configuration, such that a portion of said second auxiliary tongue is in overlapping abutting relationship with a respective portion of said second support, wherein to enhance said second support pressure. For example, each said second auxiliary tongue is connected at one end thereof to an inner end of a corresponding said second tongue, wherein at least prior to donning the body support said second auxiliary tongue is in overlying relationship with the corresponding said second tongue, and wherein said second auxiliary tongue is pivoted about said one end thereof away from the corresponding said second tongue to enable said second auxiliary tongue to be affixed with respect to said second support.

In at least some examples, in the doffed configuration the first support and the second support are permanently joined to one another exclusively via said connecting section.

In at least some examples, at least in doffed configuration said free second outer lateral end and said free second outer lateral end are unattached to one another.

In at least some examples, at least in the doffed configuration said first support and said second support are unattached directly to one another.

In at least some examples, in use of the chest support when supporting the chest, there is an absence of a permanent fixation between said free second outer lateral end and said free second outer lateral end.

In at least some examples, in the donned configuration the chest support is affixed to the chest exclusively via said first pressure and said second pressure.

In at least some examples, first support pressure results in a tightening of the chest support over the chest, at the general location of the at least one first tongue, in a predominantly lateral direction with respect to the chest.

In at least some examples, second support pressure results in a tightening of the chest support over the chest, at the general location of the at least one second tongue, in a predominantly lateral direction with respect to the chest.

In at least some examples, said at least one first tongue is in parallel transversely spaced relationship with respect to said at least one second tongue.

In at least some examples, in the donned configuration, a first edge of first outer lateral end is in abutment with a second edge of said first outer lateral end.

In at least some examples, in the donned configuration, a first edge of first outer lateral end is in abutment with a second edge of said first outer lateral end at an abutment zone in cross-over configuration, wherein to allow a first portion of said first outer lateral end to overlie a first portion of said second outer lateral end, while concurrently allowing a second portion of said second outer lateral end to overlie a second portion of said first outer lateral end.

According to the above aspects of the presently disclosed subject matter there are provided a variety of body supports for supporting a body portion, for example for supporting a chest in a donned configuration. In some examples, the body support includes a first support panel having one or more first tongues projecting outwardly therefrom, a second support panel having one or more second tongues projecting outwardly therefrom, a connecting section, joining the first support panel to said second support panel in longitudinal spaced relationship along an imaginary longitudinal midline of the body support, the first tongue and the second tongue being on opposite transverse sides of a mid-line of the body support, a first fastener and s second fastener. The body support further having a doffed configuration wherein the first support panel and the second support panel are non-contiguous with respect to one another.

A feature of at least one example of the presently disclosed subject matter is that the level of pressure that can be applied by the chest support on one breast area can be set independently from the level of pressure that can be applied by the chest support on the other breast area.

A feature of at least one example of the presently disclosed subject matter is that the level of pressure that can be applied by the chest support on one breast area can be set to be different (higher or lower) from the level of pressure that can be applied by the chest support on the other breast area.

A feature of at least one example of the presently disclosed subject matter is that the two breast areas can be concurrently supported firmly at a superior location as well as at an inferior position.

Each of these features can be of benefit, for example, after breast surgery of any kind, including medical and/or cosmetic surgeries involves surgical intervention in the breast and nearby regions and where support for the chest is required.

In some examples, such as in cases of post surgical use, the chest support can be combined with wound dressing material, such as material that absorbs exudates or other fluids exerted from post surgical incisions.

In some examples, the chest support can carry substances that facilitate wound healing.

BRIEF DESCRIPTION OF THE DRAWINGS

In order to better understand the subject matter that is disclosed herein and to exemplify how it may be carried out in practice, examples will now be described, by way of non-limiting example only, with reference to the accompanying drawings, in which:

FIG. 1 shows in back view a first example of the chest support, in laid-out configuration, i.e., when laid flat, in a doffed configuration.

FIG. 2 shows in front view the example of FIG. 1 in laid-out doffed configuration.

FIG. 9(a) shows in back view an alternative variation of the example of FIG. 1, in laid-out, doffed configuration; FIG. 9(b) shows in front view the example of FIG. 9(a), in laid-out, doffed configuration.

DETAILED DESCRIPTION

Figure 3:
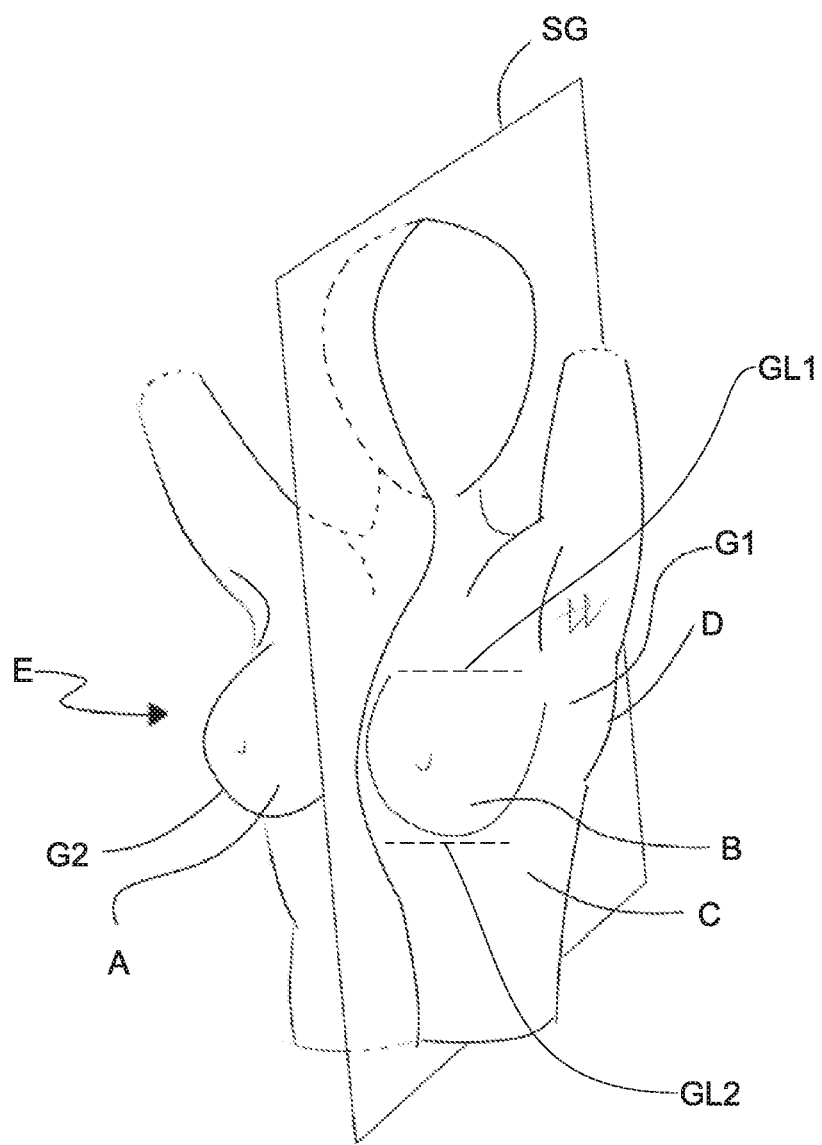
FIG. 3 schematically illustrates in partial isometric view an example of an upper torso of a female human being.

Referring to FIGS. 1 and 2, a body support according to a first example of the presently disclosed subject matter is illustrated, the body support being configured for covering and supporting a body portion. In particular, the body support is configured for covering and supporting at least a first body area and a second body area of the body portion, each one of the first body area and the second body area being on a different lateral side of a median plane of the body portion.

In this example, the body support is in the form of a chest support, the body portion being a chest of a human being. However, as will become clearer herein, variations of this example, mutatis mutandis, can be provided for covering and supporting other body portions of human beings or of animals, comprising, inter alia, for example any one of: an arm, a palm, a finger, a leg, a foot, a toe, an abdomen, a hip, a neck.

Referring again to FIGS. 1 and 2, the chest support according to this example is generally designated 100, and comprises a first support in the form of first breast support 120 (also interchangeably referred to herein as first breast support panel, or more generally as first support panel), a second support in the form of second breast support 140 (also interchangeably referred to herein as second breast support panel or more generally as second support panel), a connecting section 160, a first fastener 170 and a second fastener 190.

As will become clearer herein, the body support according to examples of the presently disclosed subject matter, in this example the chest support 100, has a donned configuration (in which the body support is fixed to the body portion, e.g. in which the chest support 100 is fixedly secured to the chest portion) and a doffed configuration (in which the body support is not affixed to the body portion and is typically removed therefrom, e.g. in which the chest support 100 is not fixedly secured to the chest portion and is typically removed therefrom).

Referring also to FIG. 3, the chest support 100 is configured for covering and supporting a first breast area A (corresponding to the first body area) and a second breast area B (corresponding to the second body area) of the chest C (corresponding to the above-mentioned body portion) of a human being, in particular a female human being. It is to be noted though that the chest support 100 according to examples of the presently disclosed subject matter can also be used coveting and supporting a corresponding first breast area and a corresponding second breast area of the chest of a male human being or of any other human being, or for some types of animals, for example at least some primates.

In the following examples, and for facilitating comprehension, the first breast area A is on the right side of the chest C and is thus also referred to herein as the right breast area A, while the second breast area B is on the left side of the chest C and is thus also referred to herein as the left breast area B. In other examples, it is possible instead for the first breast area A to relate to the left side of the chest C and for the second breast area B to relate to the right side of the chest C, mutatis mutandis.

Each breast area A, B nominally includes a respective breast, but in some cases can instead include the area of the chest C where one such breast has been partially or fully removed, for example following severe trauma or surgery, or where no breast has formed at all or is malformed (e.g. due do some birth defect), where otherwise a breast would be located. Thus, each breast area A, B, is on a different lateral side of a median plane of the body part, in particular the midsagittal plane SG of the upper torso E, including chest C.

Figure 4:
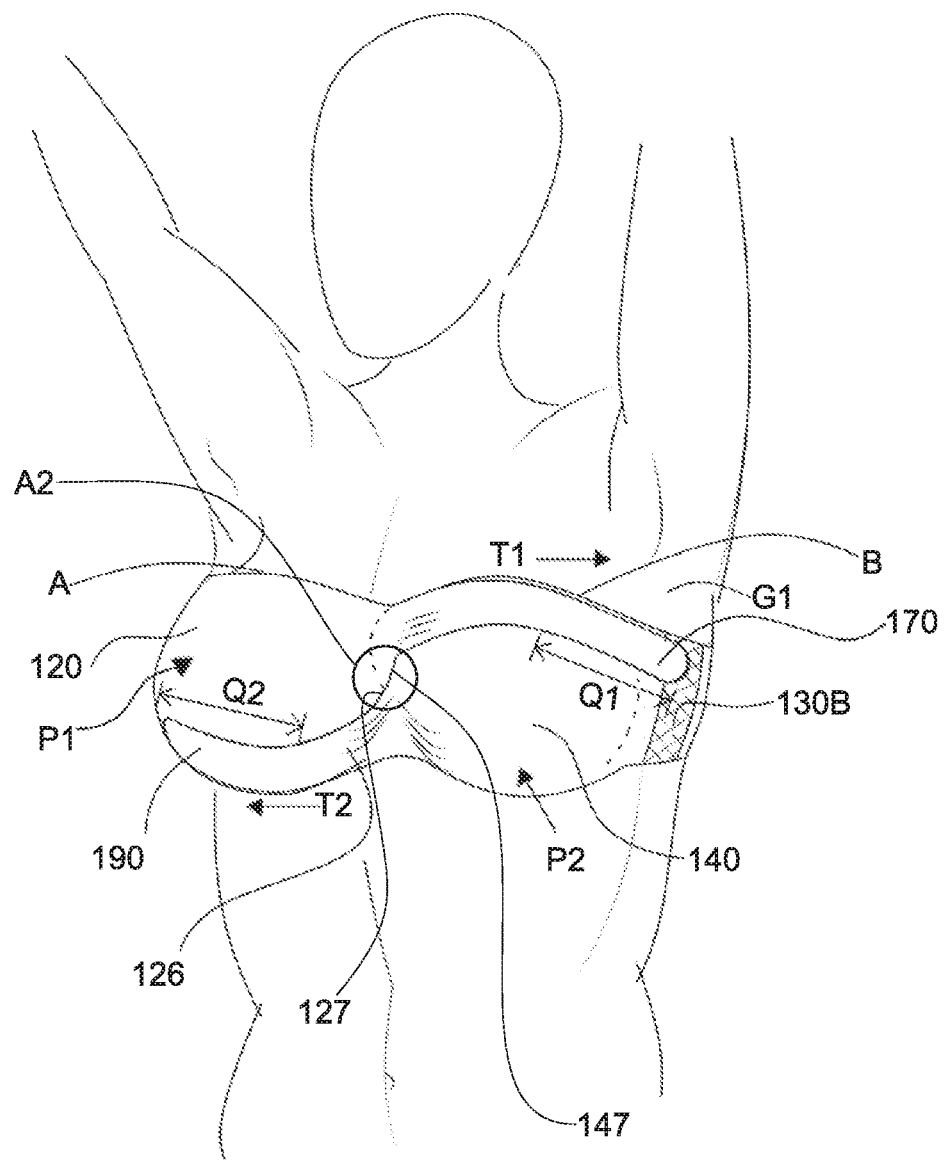
FIG. 4 illustrates in isometric view the example of FIGS. 1 and 2 in affixed, or donned configuration, affixed to the torso of FIG. 3.
Figure 4A:
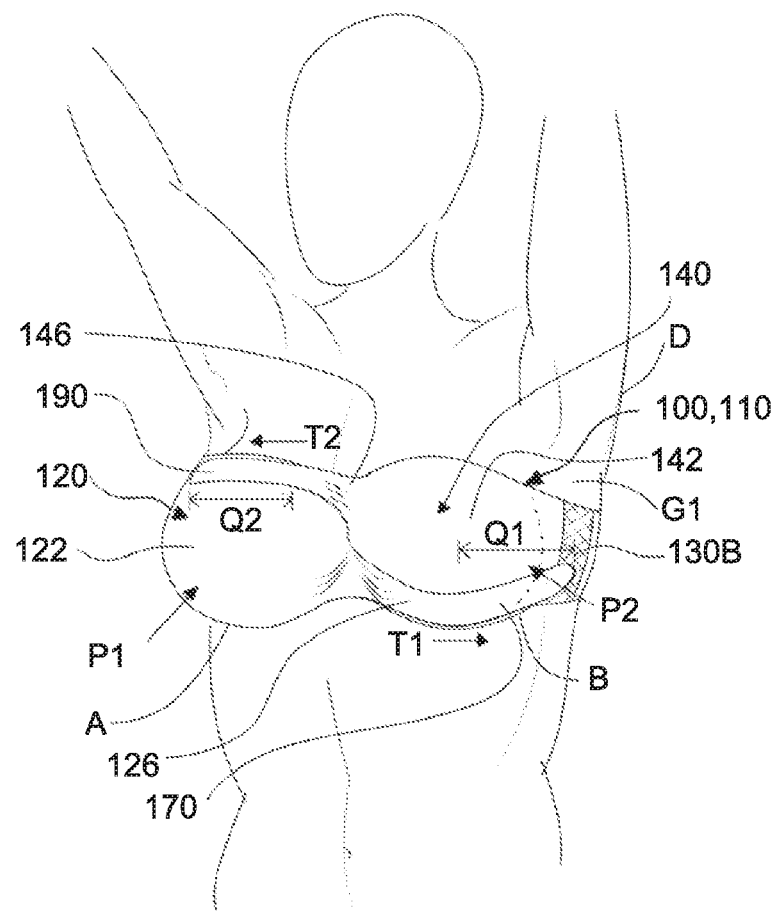
FIG. 4(a) illustrates in isometric view alternative variation of the example of FIG. 4 in affixed configuration, affixed to the torso of FIG. 3.
Figure 4B:
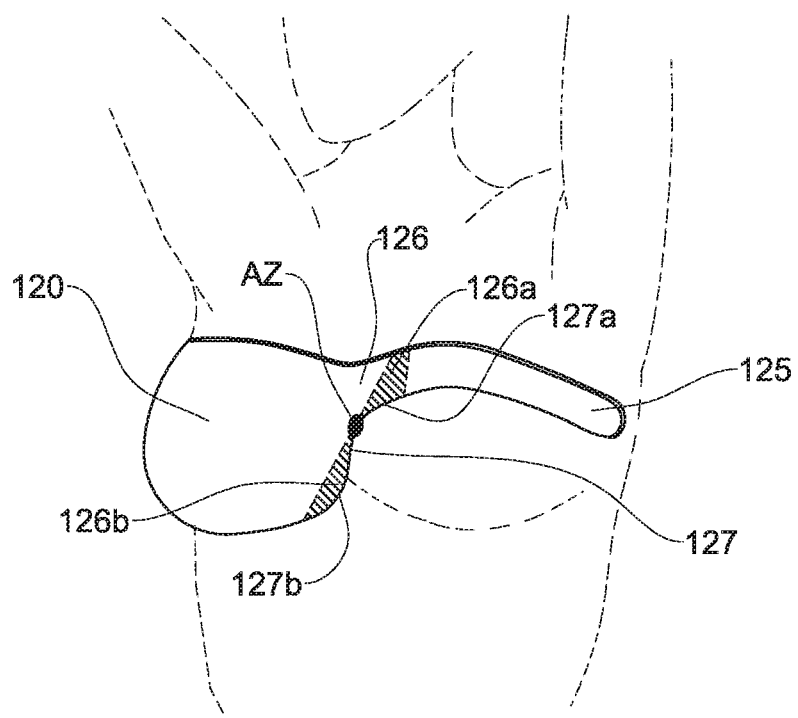
FIG. 4(b) illustrates in isometric view the example of FIG. 4, in which one breast support has been removed from this figure for clarity.
Figure 4C:
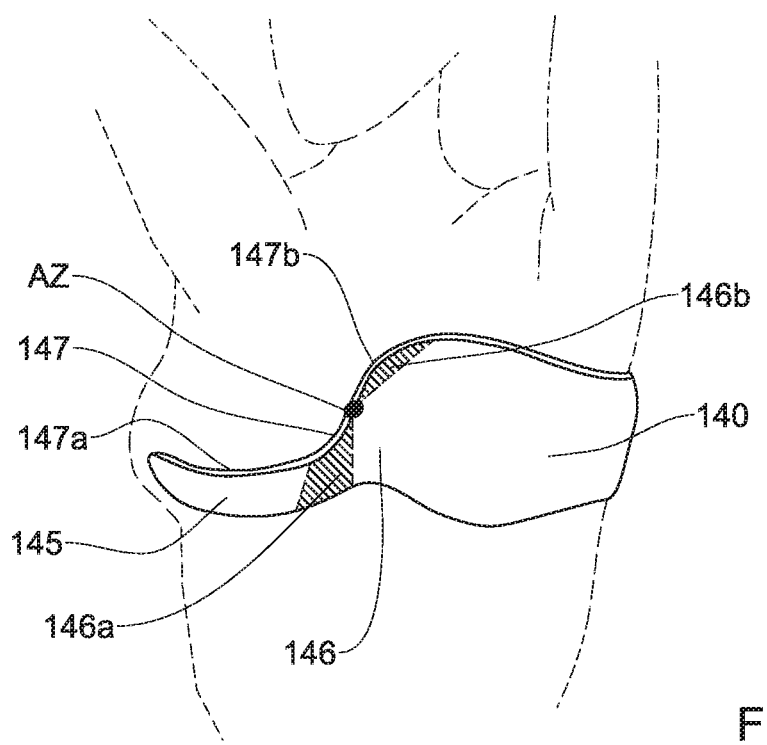
FIG. 4(e) illustrates in isometric view the example of FIGS. 4 and 4(b), in which the other breast support has been removed from this figure for clarity.

The first breast support 120 is partially or fully resilient, and comprises a resilient first breast receiving panel 122, and a first inner lateral end 124 and a flexible, free first outer lateral end 126 on opposite lateral sides of the first breast receiving panel 122. In use, and as best seen in FIG. 4, the first breast receiving panel 122 is in overlying abutting relationship (at least partially and preferably fully) with the first breast area A. Furthermore, the first breast receiving panel 122 is made from or comprises a resilient material or combination of resilient materials that applies a supporting pressure P1 to the respective first breast area A when a first tensile load T1 (also referred to interchangeably herein as a first tension) is applied to first breast receiving panel 122. Such a first tensile load T1 can be applied, for example, by pulling the free first outer lateral end 126 in a lateral direction when the first breast receiving panel 122 is in overlying abutting relationship with the first breast area A.

In some examples, such as in this example, the first breast support 120 and in particular the first breast receiving panel 122, is formed as a flat multilayered panel. However, in alternative variations of this example, the first breast support 120 and in particular the first breast receiving panel 122, can be formed with a concavity, for example can be cup-shaped, in which the inner concave surface thereof has a shape that is at least partially complementary with respect to the outer shape of the corresponding first breast area A.

The second breast support 140 is partially or fully resilient, and comprises a resilient second breast receiving panel 142, and a second inner lateral end 144 and a flexible free second outer lateral end 146 on opposite lateral sides of the second breast receiving panel 142. In use, the second breast receiving panel 142 is in overlying abutting relationship (at least partially and preferably fully) with the second breast area B. Furthermore, the second breast receiving panel 142 is also made from or comprises a resilient material or combination of resilient materials that applies a supporting pressure P2 to the respective second breast area B when a second tensile load T2 (also referred to interchangeably herein as a second tension) is applied to second breast receiving panel 142. Such a second tensile load T2 can be applied, for example, by pulling the free second outer lateral end 146 in a lateral direction when the second breast receiving panel 142 is in overlying abutting relationship with the second breast area B.

In some examples, such as in this example, the second breast support 140 and in particular the first breast receiving panel 142, is formed as a flat multilayered panel. However, in alternative variations of this example, the second breast support 140 and in particular the first breast receiving panel 142, can be formed with a concavity, for example can be cup-shaped, in which the inner concave surface thereof has a shape that is at least partially complementary with respect to the outer shape of the corresponding second breast area B.

The connecting section 160 is flexible, and connected to each one of the first breast support 120 and the second breast support 140. In use the connecting section 160 is in overlying abutting relationship (at least partially and preferably fully) with the back D of the torso E, in the donned configuration. The connecting section essentially provides mechanical continuity between the first breast support 120 and the second breast support 140, and provides a suitable spacing S between the respective first breast receiving panel 122 and the respective second breast receiving panel 142.

The serially connected first breast support 120, connecting section 160, and second breast support 140 together form a wearable covering 110, generally in the form of an elongate band having opposite free ends corresponding to the first outer lateral end 126 and the second outer lateral end 146, wherein these free ends are unattached, and non-contiguous, with respect to one another at least in the doffed configuration. The band-like covering 110 has an inner facing side 112 (FIG. 1) and an outer facing side 114 (FIG. 2), and enables the chest support 100 to encircle the torso E and to support the torso E, in the donned configuration, with the inner facing side 112 facing and generally in contact with the torso E. In particular the band-like covering 110 enables the chest support 100 to support the chest C and more particularly each of the breast areas A and B, independently from one another, when the covering 110 is in encircling relationship with the torso E and affixed to the torso E via the first fastener 170 and the second fastener 190, as will become clearer below.

The spacing S is dimensioned or otherwise configured such as to concurrently enable the first breast receiving panel 122 to be in overlying abutting relationship with the first breast area A and the second breast receiving panel 142 to be in overlying abutting relationship with the second breast area B, when the chest support 100 is encircling and supporting the torso E and the connecting section 160 is in overlying abutting relationship with the back D of the chest.

In particular, in at least this example the connecting section 160 is in the form of a flat panel or strap, and is laterally joined to the first inner lateral end 124 and to the second inner lateral end 144 via respective opposite lateral ends 162, 164 of the connecting section 160. In alternative variations of this example, the connecting section 160 can instead comprise a plurality of straps or chords, for example, joined to the first inner lateral end 124 and to the second inner lateral end 144, for example.

The first outer lateral end 126 is formed with a first tongue 125, projecting generally laterally (i.e. longitudinally) from the first breast receiving panel 122 in a direction away from the connecting section 160. The first fastener 170 is associated with the first outer lateral end 126, in particular with the first tongue 125, and at least in some examples, part or all of the first fastener 170 is affixed to the first outer lateral end 126, in particular to the first tongue 125.

Similarly, the second outer lateral end 146 is formed with a second tongue 145, projecting generally laterally from the second breast receiving panel 142 in a direction away from the connecting section 160. The second fastener 190 is associated with the second outer lateral end 146, in particular with the first tongue 125, and at least in some examples, part or all of the second fastener 190 is affixed to the second outer lateral end 146, in particular to the first tongue 125.

Thus, as the figures clearly show, and as noted above, the first outer lateral end 126 is a free end, and the second outer lateral end 146 is also a free end. Thus in the doffed configuration (for example illustrated in FIGS. 1 and 2), the first outer lateral end 126 and the second outer lateral end 146 are unattached to one another and are non-contiguous with respect to one another. It is also similarly noted that at least in some examples, in the doffed configuration the first support (for example in the form of first breast support 120) and the second support (for example in the form of second breast support 140), are permanently joined to one another exclusively, i.e., only, via said connecting section 160. In these or other examples, at least in doffed configuration the first support (for example in the form of first breast support 120) and the second support (for example in the form of second breast support 140), are unattached directly to one another. Thus, in use of the body support (in this example the chest support 100) when supporting the body portion (in this example, the chest), there is an absence of a permanent fixation between the free first outer lateral end and the free second outer lateral end; in particular there is an absence of a direct permanent fixation between the free first outer lateral end and the free second outer lateral end.

As can be seen in FIG. 2, for example, the chest support 100 also exhibits a non-symmetrical geometry with respect to a longitudinal mid-line (also interchangeably referred to herein as axis Z) of the chest support, in which the first outer lateral end 126 and the second outer lateral end 146 are on opposite transverse sides of the axis Z. In this example the first outer lateral end 126 is transversely spaced from the mid-line on a first transverse side of the mid-line, seen in this figure above the axis Z, and is configured for overlying a superior part of the corresponding breast area B, while the second outer lateral end 146 is transversely spaced from the mid-line on a second transverse side of the mid-line, seen in this figure below the axis Z, and is configured for overlying an inferior part of the corresponding breast area A, as illustrated in FIG. 4 for example. Clearly, the first transverse side and the second transverse side are opposite transverse sides of the mid-line.

It is also clear from the figures that at least in these examples, the first tongue 125 is in generally parallel transversely spaced relationship with respect to the second tongue 145.

In alternative variations of this example, the first outer lateral end 126, including the first tongue 125, can be instead provided below the axis Z and the second outer lateral end 146 including the second tongue 145, can be provided above the axis Z, in the view shown in FIG. 2, and thus, instead, the outer lateral end 126, in particular the first tongue 125, is configured for overlying an inferior part of the corresponding breast area B, while the second outer lateral end 146, in particular the second tongue 145, is configured for overlying a superior part of the corresponding breast area A, as illustrated in FIG. 4(*a*).

The first fastener 170 is configured for selectively and reversibly affixing the first outer lateral end 126 (in particular the first tongue 125) to the second breast support 140, to thereby at least partially affix the cover 110 to the torso E, i.e., in the donned configuration. In at least this example, the first outer lateral end 126 (in particular the first tongue 125) is in overlying abutting relationship with respect to the second breast support 140 when affixed thereto. Furthermore, first fastener 170 is configured for concurrently providing the first tensile load T1 to first breast receiving panel 122 when the first outer lateral end 126 (in particular the first tongue 125) is thus affixed to the second breast support 140. In particular, in at least this example, the first outer lateral end 126 (in particular the first tongue 125), or at least a portion thereof, is in overlying abutting relationship with a corresponding outer-facing portion, for example a superior outer-facing portion, of the second breast support 140 when affixed thereto.

In at least this example the chest support 100, in particular the first fastener 170 is also configured for enabling the level of the first tensile load T1 to be selectively set at any desired value, within a predetermined range of tensile load values correlated to the resilience of the first breast receiving panel 122. In at least this example, the first fastener 170 allows for the free first outer lateral end 126 (in particular the first tongue 125) to be pulled generally laterally towards the second breast support 140 when the first breast receiving panel 122 is in overlying abutting relationship with the first breast area A. The more the first outer lateral end 126 (in particular the first tongue 125) is pulled laterally towards the second breast support 140 (while maintaining the first breast receiving panel 122 in overlying abutting relationship with the first breast area A), the greater the first tensile load T1 becomes, and thus the greater the first support pressure P1 that is applied by the first breast receiving panel 122 to the first breast area A. In this situation, as the first outer lateral end 126 (in particular the first tongue 125) is pulled laterally more and more towards the second breast support 140, the first outer lateral end 126 (in particular the first tongue 125) is laterally displaced over a range of different locations Q1 over the second breast support 140 (each location Q1 in this range being incrementally further away from the first breast receiving panel 122), due to the resilience and elastic stretching of at least the first breast receiving panel 122. The first fastener 170 is configured for enabling the first outer lateral end 126 (in particular the first tongue 125) to be affixed to any one of the locations Q1 in this range, and thus when affixed to any particular such location Q1, a corresponding value of the first tensile load T1 will thus be applied to the first breast receiving panel 122. Each location Q1 corresponds to a respective relative spatial disposition between the first outer lateral end 126 and the second breast support 140.

It is also clear from the figures that at least in these examples, the first fastener 170 is operative for selectively and reversibly affixing the first tongue 125 to the second support panel at least at one relative spatial disposition on the same transverse side of the mid-line as the first tongue 125 is disposed, in this example the first transverse side of the mid-line. At each position Q1, the first outer lateral end 126 (in particular the first tongue 125), or at least a portion thereof, is in overlying abutting relationship with a corresponding outer-facing portion, for example a superior outer-facing portion, of the second breast support 140 when affixed thereto.

In at least this example the first fastener 170 comprises a first outer lateral end fastener part 172, permanently fixed to the first outer lateral end 126 (in particular to the first tongue 125), and a first breast panel fastener part 174 permanently fixed to the second breast support 140. The first outer lateral end fastener part 172 is configured for reversibly engaging with the first breast panel fastener part 174, and can take any one of many different forms. In this example, the first fastener 170 is hook-and-loop type fastener, e.g. including fasteners commonly marketed as the Velcro fasteners. Thus, the first outer lateral end fastener part 172 comprises a number of small hooks on the surface thereof which reversibly engage a plurality of small hoops provided on the outer facing surface of the first breast panel fastener part 174.

In this example, the entire outer surface of the second breast receiving panel 142, or the entire outer surface of the second breast support 140, can be formed with such small hoops, so that the first breast panel fastener part 174 correspondingly extends over the entire second breast receiving panel 142 or the entire outer surface of the second breast support 140, respectively. In this manner, the first outer lateral end fastener part 172 can be reversibly affixed at any first location Q1 over the entire outer surface of the second breast receiving panel 142 or at any first location Q1 over the entire outer surface of the second breast support 140, respectively.

In alternative variations of this example, the first breast panel fastener part 174 instead comprises a number of small hooks on the outer facing surface thereof which reversibly engage a plurality of small hoops which are instead provided on the surface of the first outer lateral end fastener part 172.

In yet other variations of this example, the first fastener 170 can take other different forms, as known per se, including for example at least some types of garment fasteners or bandage fasteners.

For example, in at least some such variations of this example the first fastener 170 comprises a button and hole fastening arrangement. For example, the first outer lateral end fastener part 172 comprises at least one button and the first breast panel fastener part 174 comprises a plurality of holes or slits formed at first positions Q1 in the second breast receiving panel 142 or in the second breast support 140, and the button is selectively engageable at any one time with any desired one of the holes/slits to thereby reversibly affix the fastener at a corresponding first position Q1. Alternatively, the first outer lateral end fastener part 172 comprises at least one hole or slit and the first breast panel fastener part 174 comprises a plurality of buttons formed at first positions Q1 in the second breast receiving panel 142 or in the second breast support 140, mutatis mutandis. In other alternative variations of this example, the first fastener 170 can comprise one or more of: snap fasteners (also known as press studs, poppers, snaps, or tiches); hook and eye fasteners; belt buckle type fasteners; and so on. In yet other alternative variations of this example, the first outer lateral end fastener part 172 and the first breast panel fastener part 174 each comprises a length of string or the like, and the two strings can be tied in a knot.

In other alternative variations of this example, the first fastener 170 is an independent fastener, and thus is independent of the first outer lateral end 126 (in particular independent of the first tongue 125) and/or of the second breast support 140, and is not permanently affixed to either, at least prior to the fastening operation. For example, the first fastener 170 in the form of an independent fastener can comprise any one of a safety pin, a suitable bandage clip, an adhesive tape, that can be concurrently engaged to both the first outer lateral end 126 (in particular the first tongue 125) and of the second breast support 140 to thereby reversibly affix these two components together responsive to the fastening operation.

The second fastener 190 is similar to the first fastener 170, and is configured for selectively and reversibly affixing the second outer lateral end 146 (in particular the second tongue 145) to the first breast support 120, to thereby at least partially affix the cover 110 to the torso E in the donned configuration. In at least this example, the second outer lateral end 146 (in particular the second tongue 145) is in overlying abutting relationship with respect to the first breast support 120 when affixed thereto, in the donned configuration. Furthermore, second fastener 190 is configured for concurrently providing the second tensile load T2 to second breast receiving panel 142 when the second outer lateral end 146 (in particular the second tongue 145) is thus affixed to the first breast support 120. In particular, in at least this example, the second outer lateral end 146 (in particular the second tongue 145), or at least a portion thereof, is in overlying abutting relationship with a corresponding outer-facing portion, for example an inferior outer-facing portion, of the first breast support 120 when affixed thereto.

In at least this example the chest support 100, in particular the second fastener 190 is also configured for enabling the level of the second tensile load T2 to be selectively set at any desired value (and independently of the level of the first tensile load T1), within a predetermined range of tensile load values correlated to the resilience of the second breast receiving panel 142. In at least this example, the second fastener 190 allows for the free second outer lateral end 146 (in particular the second tongue 145) to be pulled laterally towards the first breast support 120 when the second breast receiving panel 142 is in overlying abutting relationship with the second breast area B. The more the second outer lateral end 146 (in particular the second tongue 145) is pulled laterally towards the first breast support 120 (while maintaining the second breast receiving panel 142 in overlying abutting relationship with the second breast area B), the greater the second tensile load T2 becomes, and thus the greater the second support pressure P2 that is applied by the second breast receiving panel 142 to the second breast area B. In this situation, as the second outer lateral end 146 (in particular the second tongue 145) is pulled generally laterally more and more towards the first breast support 120, the second outer lateral end 146 (in particular the second tongue 145) is laterally displaced over a range of different locations Q2 over the first breast support 120 (each location Q2 in this range being incrementally further away from the second breast receiving panel 142), due to the resilience and elastic stretching of at least the second breast receiving panel 142. The second fastener 190 is configured for enabling the second outer lateral end 146 (in particular the second tongue 145) to be affixed to any one of the locations Q2 in this range, and thus when affixed to any particular such location Q2, a corresponding value of the second tensile load T2 will thus be applied to the second breast receiving panel 142. Each location Q2 corresponds to a respective relative spatial disposition between the second outer lateral end 146 (in particular the second tongue 145) and the first breast support 120.

It is also clear from the figures that at least in these examples, the second fastener in 190 is operative for selectively and reversibly affixing the second tongue 145 to the first support panel at least at one first relative spatial disposition on the same transverse side of the mid-line as the second tongue 145 is disposed, in this example the second transverse side of the mid-line.

At each position Q2, the second outer lateral end 146 (in particular the second tongue 145), or at least a portion thereof, is in overlying abutting relationship with a corresponding outer-facing portion, for example an inferior outer-facing portion, of the first breast support 120 when affixed thereto.

In at least this example the second fastener 190 comprises a second outer lateral end fastener part 192, permanently fixed to the second outer lateral end 146 (in particular to the second tongue 145), and a second breast panel fastener part 194 permanently fixed to the first breast support 120. The second outer lateral end fastener part 192 is configured for reversibly engaging with the second breast panel fastener part 194, and can take any one of many different forms. In this example, the second fastener 190 is hook-and-loop type fastener, e.g. including fasteners commonly marketed as the Velcro fasteners. Thus, the second outer lateral end fastener part 192 comprises a number of small hooks on the surface thereof which reversibly engage a plurality of small hoops provided on the outer facing surface of the second breast panel fastener part 194.

In this example, the entire outer surface of the first breast receiving panel 122, or the entire outer surface of the first breast support 120, can be formed with such small hoops, so that the second breast panel fastener part 194 correspondingly extends over the entire first breast receiving panel 122 or the entire outer surface of the first breast support 120, respectively. In this manner, the second outer lateral end fastener part 192 can be reversibly affixed at any second location Q2 over the entire outer surface of the first breast receiving panel 122 or at any second location Q2 over the entire outer surface of the first breast support 120, respectively.

In alternative variations of this example, the second breast panel fastener part 194 instead comprises a number of small hooks on the outer facing surface thereof which reversibly engage a plurality of small hoops which are instead provided on the surface of the second outer lateral end fastener part 192.

In yet other variations of this example, the second fastener 190 can take other different forms, as known per se, including for example at least some types of garment fasteners or bandage fasteners.

For example, in at least some such variations of this example the second fastener 190 comprises a button and hole fastening arrangement, for example as disclosed above for the first fastener, mutatis mutandis. In other alternative variations of this example, the second fastener 190 can comprise one or more of: snap fasteners (also known as press studs, poppers, snaps, or tiches); hook and eye fasteners; belt buckle type fasteners; and so on. In yet other alternative variations of this example, the second outer lateral end fastener part 192 and the second breast panel fastener part 194 each comprises a length of string or the like, and the two strings can be tied in a knot.

In other alternative variations of this example, the second fastener 190 is an independent fastener, and thus is independent of the second outer lateral end 146 and/or of the first breast support 120, and is not permanently affixed to either, at least prior to the fastening operation, for example as disclosed above for the first fastener, mutatis mutandis.

Thus, in this example, and in other examples, in the donned configuration the body support (in this example the chest support 100) is affixed to the body portion (in this example, the chest), exclusively via the first support pressure and the second pressure, without the necessity for additional supporting braces or other support structures (for example without the need for shoulder straps etc). Furthermore, in this example, and in other examples, it is also clear that the first support pressure results in a tightening of the body support (in this example, of the chest support 100) over the body portion (in this example, the chest), at the general location of the first tongue, in a predominantly lateral direction with respect to the body portion (for example indicated at GL1 in FIG. 3). Furthermore, in this example, and in other examples it is also clear that the second support pressure results in a tightening of the body support (in this example, of the chest support 100) over the body portion (in this example, the chest), at the general location of the second tongue, in a predominantly lateral direction with respect to the body portion (for example indicated at GL2 in FIG. 3).

In this example, the first tongue 125 is transversely spaced with respect to the second tongue 145 by a transverse spacing, wherein said transverse spacing is generally not less than a height dimension associated with the breast areas.

Referring to FIGS. 2 and 4, 4(*b*), 4(*c*) for example, in the donned configuration, a first edge 127 of first outer lateral end 126 is in abutment with a second edge of said first outer lateral end 146. Furthermore, and as best seen in FIG. 4, in the donned configuration, the first edge 126 is in abutment with the second edge 146 at an abutment zone AZ in "cross-over configuration". Herein "cross-over configuration" refers to an abutment between these two edges wherein the edges are not perfectly co-aligned, and thereby allow for a cross-over of some parts of each of the two breast supports 120, 140 to lie above and other parts of the two breast supports to lie below the other breast support. For example, referring to FIG. 4 together with FIGS. 4(*b*) and 4(*c*), the first edge 127 can be divided into two parts, 127*a*, 127*b* which come together at the abutment zone AZ. Edge part 127*a* extends along the first tongue 125 and overlies the second breast support 140, while edge part 127*b* is overlaid by a part of the second breast support 140. Similarly, the second edge 147 can be divided into two parts, 147*a*, 147*b* which come together at the abutment zone AZ. Edge part 147*a* extends along the second tongue 125 and overlies the first breast support 120, while edge part 147*b* is overlaid by a part of the first breast support 120. In other words, the resulting cross-over configuration by the abutment of edges 127, 147 allows a first portion 126*a* of said first outer lateral end 126 to overlie a second portion 146*b* of said second outer lateral end 146, while concurrently allowing a first portion 146*a* of said second outer lateral end 146 to overlie a second portion 126*b* of said first outer lateral end 126.

Without being bound by theory, this cross-over configuration allows for pulling the first tongue 125 to generate the first tensile load T1 which is concurrently resisted by second edge 147 during the donning procedure, to thereby set the desired first pressure P1, and further allows independently for the pulling of the second tongue 145 to generate the second tensile load T2 which is concurrently resisted by first edge 127 during the donning procedure, to thereby set the desired second pressure P2.

Figure 15A:
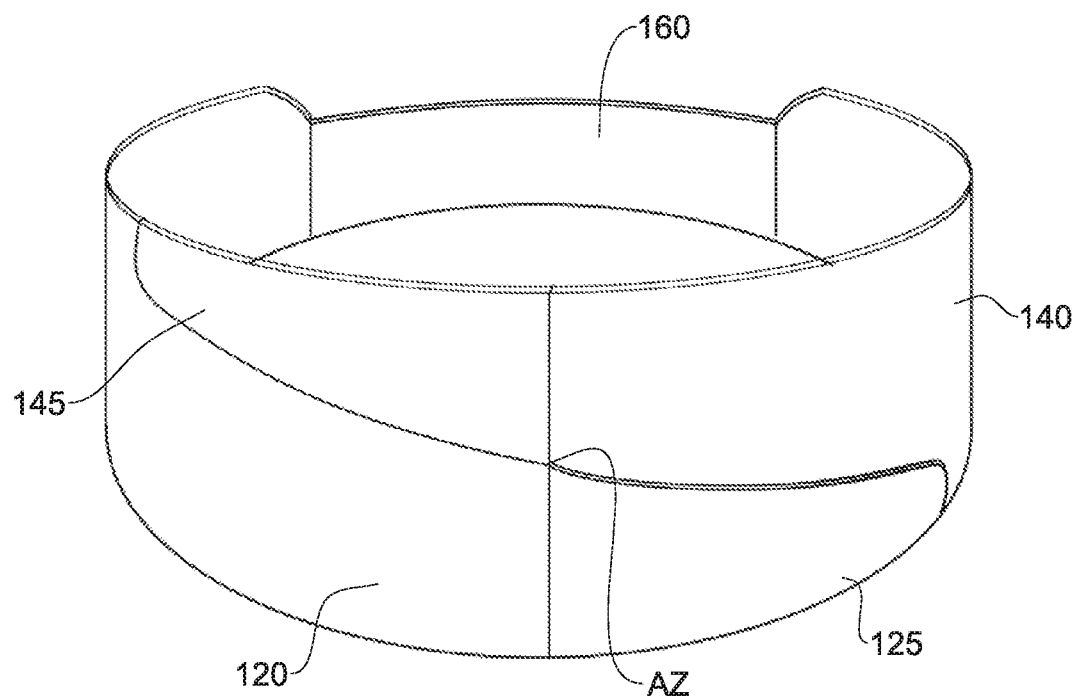
FIG. 15(a) shows in isometric front view another alternative variation of the example of FIG. 1, in affixed, donned configuration.
Figure 15B:
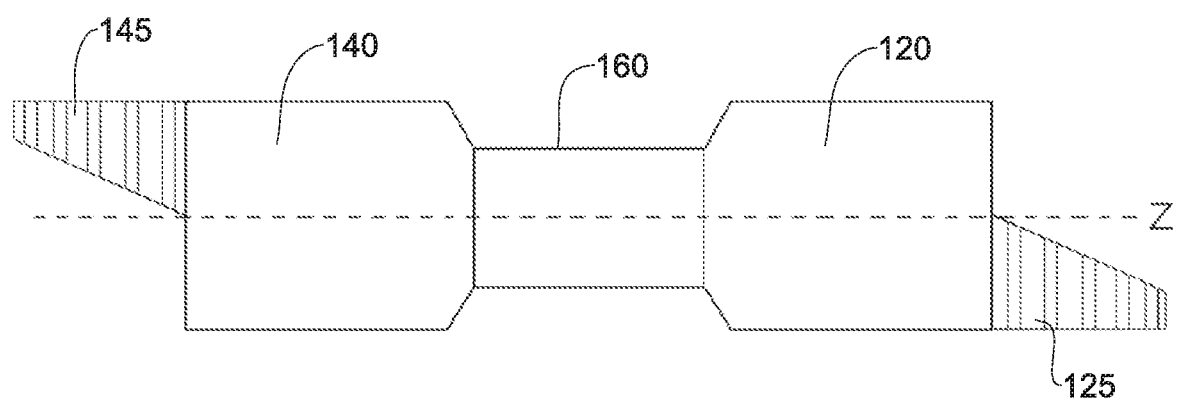
FIG. 15(b) shows in front view the example of FIG. 13(a), in laid-out, doffed configuration.

Referring to FIGS. 15(a) and 15(b), in an alternative variation of the example of FIGS. 1 and 2, the abutment zone AZ is further emphasized and more discretely defined, by providing the first tongue 125 and the second tongue 145 that transversely extend inwardly at their roots up to the mid-line or Z-axis.

In this example, the chest support 100 further comprises a first auxiliary fastener 180 for reversibly affixing together the first breast support 120 and the second breast support 140 at an anterior position with respect to the chest C, in particular a generally medial anterior position, generally corresponding to the midsagittal plane SG. This position generally corresponds to the abutment zone AZ. Without being hound to theory, inventor considers that at least in some cases, engaging together the first breast support 120 and the second breast support 140 via the first auxiliary fastener 180 can facilitate subsequent affixing operation of the first fastener 170 and/or affixing operation of the second fastener 190.

In this example, the first auxiliary fastener 180 comprises a first breast support tiff fastener part 182, permanently fixed to the first breast support 120, and a second breast support fastener part 184, permanently fixed to the second breast support 140. The first breast support fastener part 182 is configured for reversibly engaging with the second breast support fastener part 184. The second breast support fastener part 184 is defined on a fastener area 185 on the outer facing side 114 of the band-like covering 110, in particular located on the outer facing surface of the second breast support 140.

In this example, the first breast support fastener part 182 is provided on a tongue or tab 183 that projects outwardly from the first breast support 120 in a lateral direction away from the connecting section 160. The tab 183 is generally similar in shape to the fastener area 185, and is located with respect to the first breast support 120 in a manner such that when the tab 183 is in overlapping relationship with fastener area 185, the first breast support fastener part 182 is engaged to the second breast support fastener part 184. Furthermore, the covering 110 is configured (for example by having the appropriate longitudinal length and/or being sufficiently pliable and/or stretchable) to provide such an overlapping relationship concurrently with the covering 110 encircling and snugly abutting the torso E.

The first auxiliary fastener 180, and indeed the first breast support fastener part 182 and the second breast support fastener part 184, can take any one of many different forms, for example as disclosed above for the first fastener 170, the first outer lateral end fastener part 172 and the first breast panel fastener part 174, respectively, mutatis mutandis. For example, the first auxiliary fastener 180 is hook-and-loop type fastener, e.g. including fasteners commonly marketed as the Velcro fasteners, in which first breast support fastener part 182 comprises a number of small hooks on the surface thereof which reversibly engage a plurality of small hoops provided on the outer facing surface of the second breast support fastener part 184, or vice versa. Alternatively, as already mentioned, the first auxiliary fastener 180 can instead include, for example, any garment fasteners or bandage fasteners, including for example any one of: button and hole fasteners; snap fasteners; hook and eye fasteners; belt buckle type fasteners; string fasteners; independent fasteners.

Referring to FIGS. 9(a) and 9(b), in an alternative variation of the first example, the tab 183 has an S-shape closely following the profile of part of the periphery of the outer lateral end 126 generally similar in shape to the S-shaped fastener area 185. In a similar manner to the example of FIGS. 1 and 2, fastener area 185 is located with respect to the first breast support 120 in a manner such that when the tab 183 is in overlapping relationship with fastener area 185, the first breast support fastener part 182 is engaged to the second breast support fastener part 184. In this example, the first breast support fastener part 182 is engaged to the second breast support fastener part 184 in a similar manner to that disclosed for the example of FIGS. 1 and 2, mutatis mutandis, for example including hook-and-loop type fastener.

In this example, the chest support 100 further comprises a second auxiliary fastener 188 for reversibly affixing together the first breast support 120 and the second breast support 140 at an anterior position with respect to the chest C, generally corresponding to the midsagittal plane SG. Without being bound to theory, inventor considers that at least in some cases, engaging together the first breast support 120 and the second breast support 140 via the second auxiliary fastener 188 can facilitate providing a contiguous covering of the two breast areas A and B.

In this example, the second auxiliary fastener 188 comprises any suitable fastener arrangement, for example as disclosed herein for the first auxiliary fastener 180, mutatis mutandis.

In alternative variations of this example, the first auxiliary fastener 180 and/or the auxiliary fastener 188 can be omitted from the chest support 100.

In this example, and referring in particular to FIGS. 2, 3 and 4, the chest support 100 further comprises a pair of stabilizing panels 130A, 130B, configured to be in overlying relationship with the left side G1 of the upper rib cage and the right side G2 the upper rib cage, respectively, when the covering 110 is encircling and snugly abutting the torso E.

The stabilizing panels 130A, 130B are located at opposite lateral ends 162, 164, respectively, of the connecting section 160. The stabilizing panels 130A, 130B are generally flexible but non-elastic (i.e. essentially non- or only minimally stretchable), at least in a lateral direction, and thus do not significantly stretch (particularly elastically) at least in the lateral direction, when subjected to a lateral tensile load, i.e. as compared with the stretching of the first breast receiving panel 122, the second breast receiving panel 142, and/or the connecting section 160 when these are subjected to the same tensile load.

The stabilizing panels 130A, 130B thus effectively isolate or separate any stretching of the connecting section 160 from any stretching of the first breast support 120 and/or of the second breast support 140, for example when the covering 110 encircling and snugly abutting the torso E, and tensile loads are applied to first breast support 120 and/or of the second breast support 140. Furthermore, and depending on the physiological size of the back D and chest C of a particular user, it is possible to stretch the connecting section 160 by a desired amount such as to align the stabilizing panels 130A, 130B with the left side G1 of the upper rib cage and the right side G2 the upper rib cage, respectively, and then with the stabilizing panels 130A, 130B at these positions, the remainder of the chest support 100 is affixed and adjusted to provide the desired levels of pressure P1 and P2 to each of the chest areas A, B.

Furthermore, the stabilizing panels 130A, 130B can also be used for stabilizing drainage tubes and the like with respect to the torso E, for example by engaging a part of such tubes to one or another of the stabilizing panels 130A, 130B. For example stabilizing drainage tubes can be provided by sandwiching the corresponding part of the respective tube between the torso E and one or another of the stabilizing panels 130A, 130B, and/or by providing one or more engagement/clamping devices on the stabilizing panels 130A, 130B for engaging or clamping the tubes thereon.

In some examples, stabilizing panels 130A, 130B are made from a non-resilient and/or non-stretchable material, albeit flexible material. The stabilizing panels 130A, 130B are, in accordance with some examples, permanently affixed to the connecting section 160 and optionally also to the respective first breast support 120 and/or of the second breast support 140, for example via stitching.

In alternative variations of this example, the stabilizing panels 130A, 130B are made from resilient or otherwise stretchable materials, and are permanently affixed to the connecting section 160 and optionally also to the respective first breast support 120 and/or of the second breast support 140, in a non-stretchable or non-resilient manner, for example via stitching using a non-resilient and/or non-stretchable stitching material, welding, gluing, or otherwise treating the material to become none or minimally elastic. In yet other alternative variations of this example, the stabilizing panels 130A, 130B are integrally formed with the connecting section 160, and made from the same materials. In such cases the areas the connecting section 160 corresponding to the stabilizing panels 130A, 130B comprises a pattern made from a non-resilient or non-stretchable material that reduces the elasticity of the stabilizing panels 130A and 130. The pattern is such as to effectively prevent these areas from stretching (particularly elastically), at least laterally, when subjected to a lateral tensile load. For example, such a pattern includes portions aligned along, or parallel with, the axis Z. For example, the pattern can be a Zig-Zag stitching at the desired area to cause the area to become more firm/less stretchable.

In alternative variations of this example, the stabilizing panels 130A, 130B can be omitted from the chest support 100.

In this example, and referring again to FIG. 4, the first breast support 120 and the second breast support 140 are formed with the same or similar resilience, i.e., they each provide the same level of support pressure P1, P2, respectively, when subjected to similar levels of tensile loads T1, T2. However, in alternative variations of this example, the first breast support 120 and the second breast support 140 can be formed with significantly different resilience, one from the other, and thus they each provide a significantly different level of support pressure P1, P2, respectively, when subjected to similar levels of tensile loads T1, T2. In yet other alternative variations of this example and in other examples, one of the first breast support 120 and the second breast support 140 can be formed without significant resilience, while the other one of the first breast support 120 and the second breast support 140 is formed with significant resilience, such that a corresponding one the two breast supports does not provide any significant level of support pressure while the other breast support does provide a significantly level of support pressure, respectively, when subjected to similar levels of tensile loads T1, T2.

In yet other alternative variations of this example and in other examples, the level of tension T1 (and thus support pressure P1) and/or the level of tension T2 (and thus support pressure P2) can each be pre-set at a single respective value that cannot be changed. For example, the first fastener 170 is configured for securing/affixing the first outer lateral end 126 to a single position Q1, and/or the second fastener 190 is configured for securing/affixing the second outer lateral end 146 to a single position Q2.

In any one of the examples herein, the level of tension T1 (and thus support pressure P1) can be the same as the level of tension T2 (and thus support pressure P2), or alternatively, the level of tension T1 (and thus support pressure P1) can be different from the level of tension T2 (and thus support pressure P2).

In some examples, the chest support is manufactured as a single piece where portions corresponding to the different functional elements of the chest support 100, e.g. connection section, stabilizing panel, breast support, etc. are treated or manipulated in a manner to provide the respective portion with the required resilience and/or flexibility and/or firmness. In some other examples, the chest support is manufactured from distinct panels, and during the manufacturing process, the distinct panels connected into a single piece. Such panels can be connected by any means available in the textile or other industry, including stitching, welding, gluing, etc.

In yet some examples, at least part of the chest support 100 is in laminate form. For example, each one of the first breast support 120 and the second breast support 140 can comprise one or more layers of absorbing materials. This can be, without being limited thereto, for the purpose of allowing absorption of secretions, e.g. when the support is used post surgery. A multi-laminate chest support can be manufactured in stages, as illustrated in the non-limiting example of FIGS. 5(a) to 5(d).

Figure 5A:
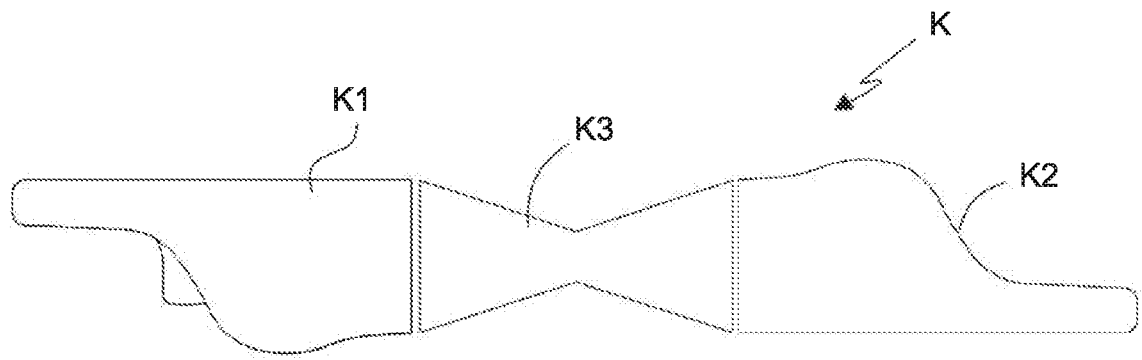
FIG. 5(a), FIG. 5(b), FIG. 5(c), FIG. 5(d), FIG. 5(e), and FIG. 5(f) illustrate first, second, third, fourth, fifth, and sixth steps, respectively in the manufacture of the example of FIG. 1, according to one manufacturing example.

Referring to FIG. 5(a), in a first stage of a manufacturing example, a first layer K of the chest support 100 is provided by laterally joining three panels K1 (corresponding to the first breast support 120), K2 (corresponding to the second breast support 140), and K3 (corresponding to the connecting section 160), all three panels can be made from the same or different material. In some examples, such as when manufacturing a multi-layered support, the three panels are typically made of the same material. Such a material would be plaint and resilient, and enables the applied pressures P1 and P2 to be generated in response to the applied tensile stresses T1, T2.

Figure 5B:
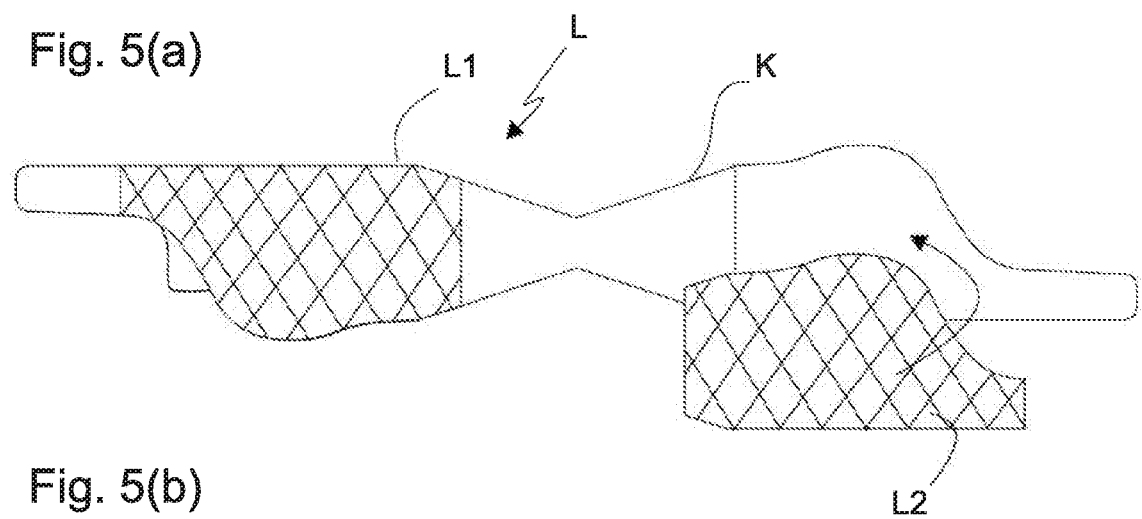

Referring to FIG. 5(b), a second stage of a manufacturing example, a second layer L of the chest support 100 is provided by overlappingly joining two panels L1 and L2 over parts of first layer K. Panel L1 is overlaid on a majority of panel K1 (corresponding to most of the first breast support 120 including at least the first breast receiving panel 122), while panel L2 is overlaid on a majority of panel K2 (corresponding to most of the second breast support 140 including at least the second breast receiving panel 142). In this example panels L1 and L2 are made from the same material; though in alternative variations of this example and in other examples, each one of the panels L1 and L2 is made from a different material. In some examples, panels L1 and L2 are used to absorb secretion from or to release substances to the subject's skin. Such a material for one or each of the panels L1 and L2 can be cotton cellulose gauze formed as a woven or nonwoven sheet.

Figure 5C:
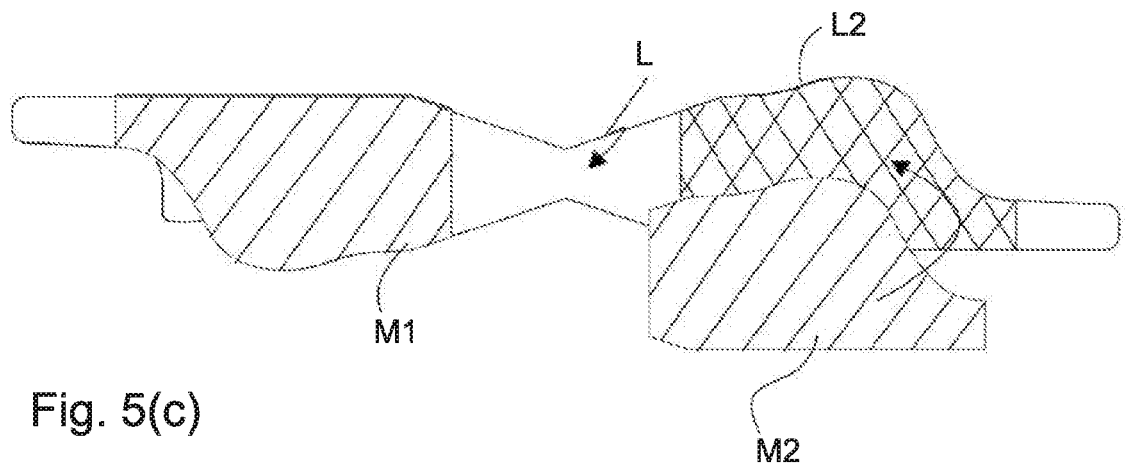
Figure 5D:
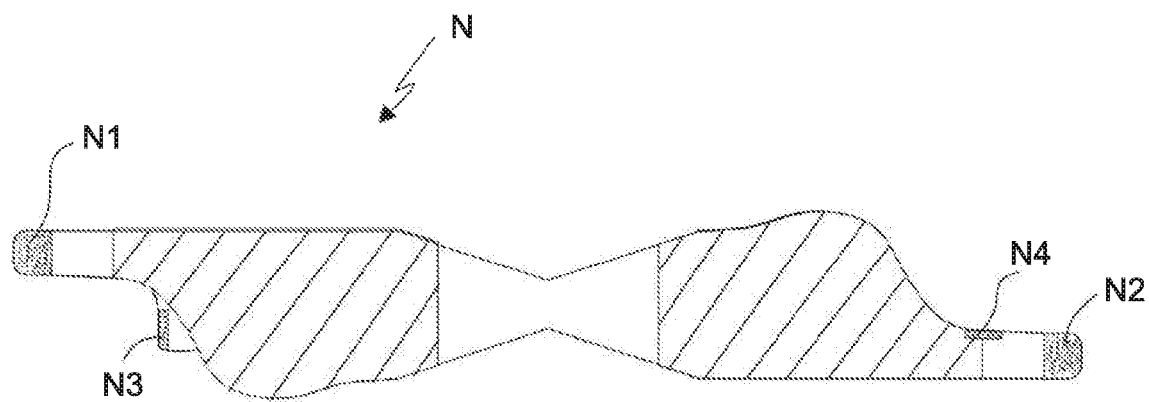
Figure 5E:
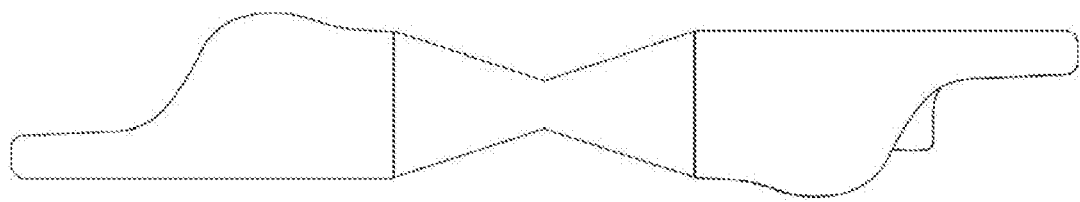
Figure 5F:
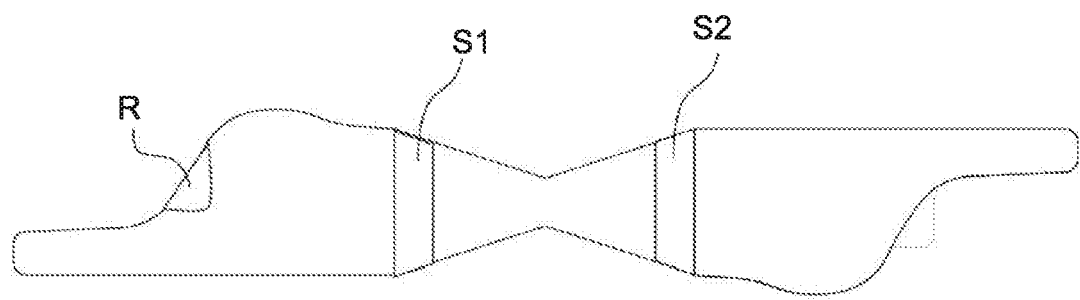

Referring to FIG. 5(c), in a third stage of a manufacturing example, a third layer M of the chest support 100 is provided by overlappingly joining two panels M1 and M2 over panels L1 and L2, respectively. Thus, panel M1 is also overlaid on a majority of panel K1 (corresponding to most of the first breast support 120 including at least the first breast receiving panel 122), and panel M2 is also overlaid on a majority of panel K2 (corresponding to most of the second breast support 140 including at least the second breast receiving panel 142). In this example, panels M1 and M2 are made from the same material; though in alternative variations of this example and in other examples, each one of the panels M1 and M2 is made from a different material. Such a material for one or each of the panels M1 and M2 is configured for being in direct contact with the breast areas A and B, and for providing comfort feeling to the subject.

It is to be noted that layers L and M do not prevent (and are thus configured for not preventing) the panels K1 and K2 from applying pressures P1 and P2 in response to the applied tensile stresses T1, T2, in use of the chest support 100.

Referring to FIG. 5(*d*), in a fourth stage of the first manufacturing example, a plurality of fastener portions N are affixed to the laminated article produced in FIG. 5(*c*). Fastener portions N include:

fastener portion N1, corresponding to first outer lateral end fastener part 172;
fastener portion N2, corresponding to second outer lateral end fastener part 192;
fastener portion N3, corresponding to first breast support fastener part 182;
fastener portion N4, corresponding to a portion of second auxiliary fastener 188.

Referring to FIG. 5(*e*), in a fifth stage of a manufacturing example, the laminated article produced in FIG. 5(*d*) is turned over.

Referring to FIG. 5(*f*), in a sixth stage of a manufacturing example, portions R, S1 and S2 are overlaid and affixed to the laminated article produced in FIG. 5(*d*), having already been turned over. Portion R corresponds to second breast support fastener part 184, while portions S1 and S2 correspond to stabilizing portions 130B and 130A, respectively.

It is of course evident that in alternative variations of this manufacturing example, the turning step illustrated in FIG. 5(*e*) can be omitted (and step illustrated in FIG. 5(*f*) is performed by appropriately holding the laminated article produced in FIG. 5(*d*)), and/or the step illustrated in FIG. 5(*f*) can optionally be performed at any time, from prior to the step illustrated in FIG. 5(*a*) to after the step illustrated in FIG. 5(*d*). It is also readily evident that in alternative variations of this manufacturing example, the step illustrated in FIG. 5(*f*) can be omitted, for example in examples where stabilizing portions 130B and 130A are not required (and thus step illustrated in FIG. 5(*e*) is also omitted).

It is appreciated that alternative examples of a chest support 100 can be performed using the same or only some of the stages outlined above. For example, a single layer support can be obtained by omitting the second and third stages.

In at least this example, the chest support 100 is provided as a disposable article. By disposable is meant that the chest support 100 is not intended to be washed or otherwise refurbished after use with a particular user; rather, after a single use (or after a small number of uses by the user) the chest support 100 is disposed of or otherwise discarded, and not used again.

In alternative variations of the above examples, the chest support 100 is provided as a non-disposable article, in which the article can be washed or otherwise refurbished between uses. For example, such a chest support can be formed from one or a plurality of suitable fabrics, and optionally can comprise disposable or washable pads on the inner side 112 of the chest support, on each one of the first breast receiving panel 122 and the second breast receiving panel 142. Optionally, such pads can be reversibly mounted to the first breast receiving panel 122 and the second breast receiving panel 142, to facilitate the replacement of the pads. Optionally, such pads can be formed from absorbent materials to absorb exudates or other bodily fluids that can come into contact therewith. Optionally, such pads can be impregnated with a suitable agent for application of the agent to the respective breast areas A, B by contact therewith.

The chest support 100 can be operated, i.e., donned or doffed, for example as follows.

Figure 6:
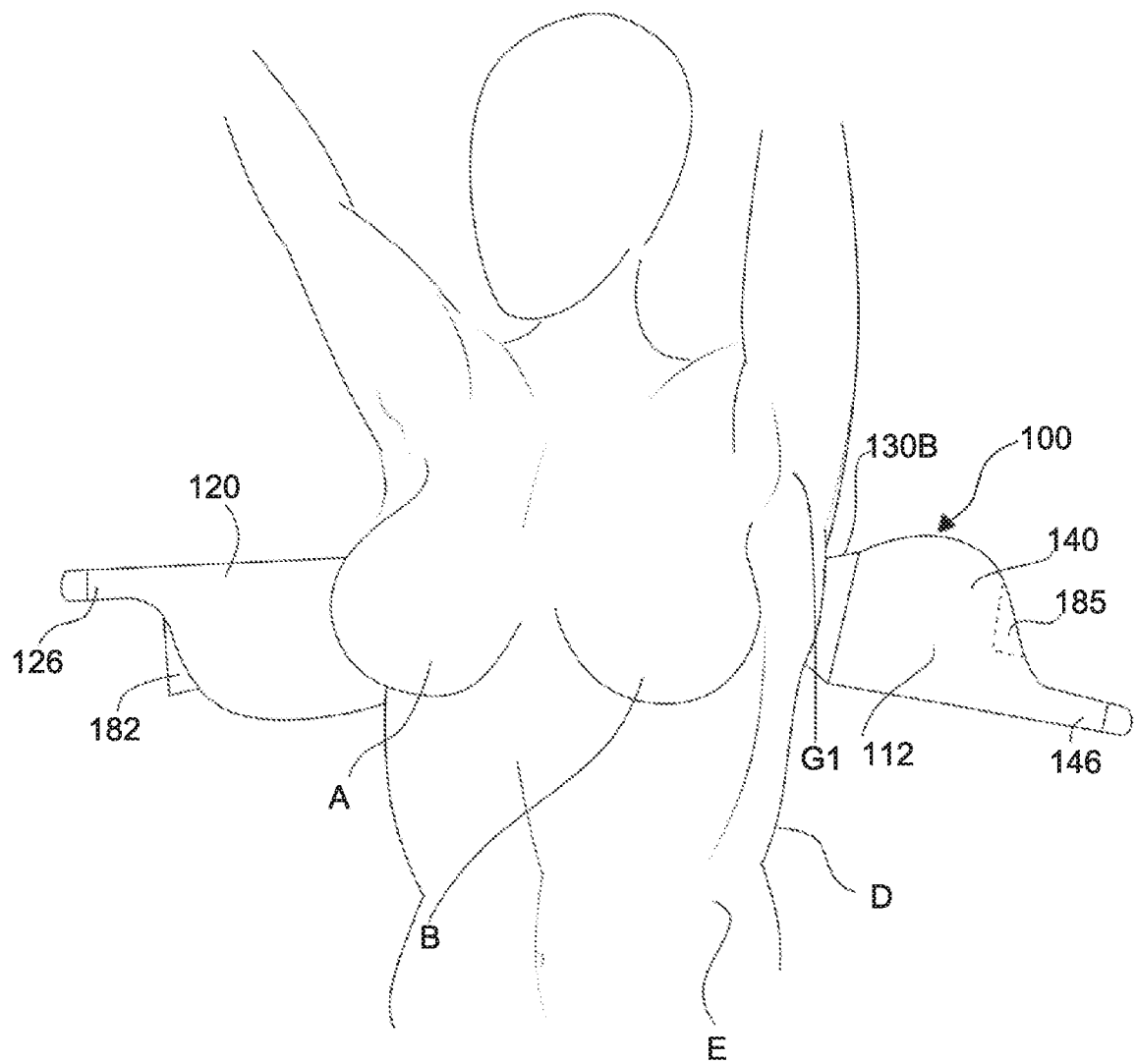
FIG. 6 illustrates in isometric view the example of FIGS. 1 and 2 prior to being affixed/donned to the torso of FIG. 3.

Referring to FIGS. 6, 7, 8 and 4, the chest support 100 can be donned or otherwise put on the torso E, for example as follows. Referring to FIG. 6, the chest support 100 is brought into proximity with the torso E, with the inner facing side 112 facing the back D, and then the connecting section 160 is brought into abutting contact with the back D. The stabilizing panels 130A, 130B, are brought into overlying relationship with the left side G1 of the upper rib cage and the right side G2 the upper rib cage, respectively, and if necessary, the connecting section 160 can be stretched laterally to accomplish this.

Figure 7:
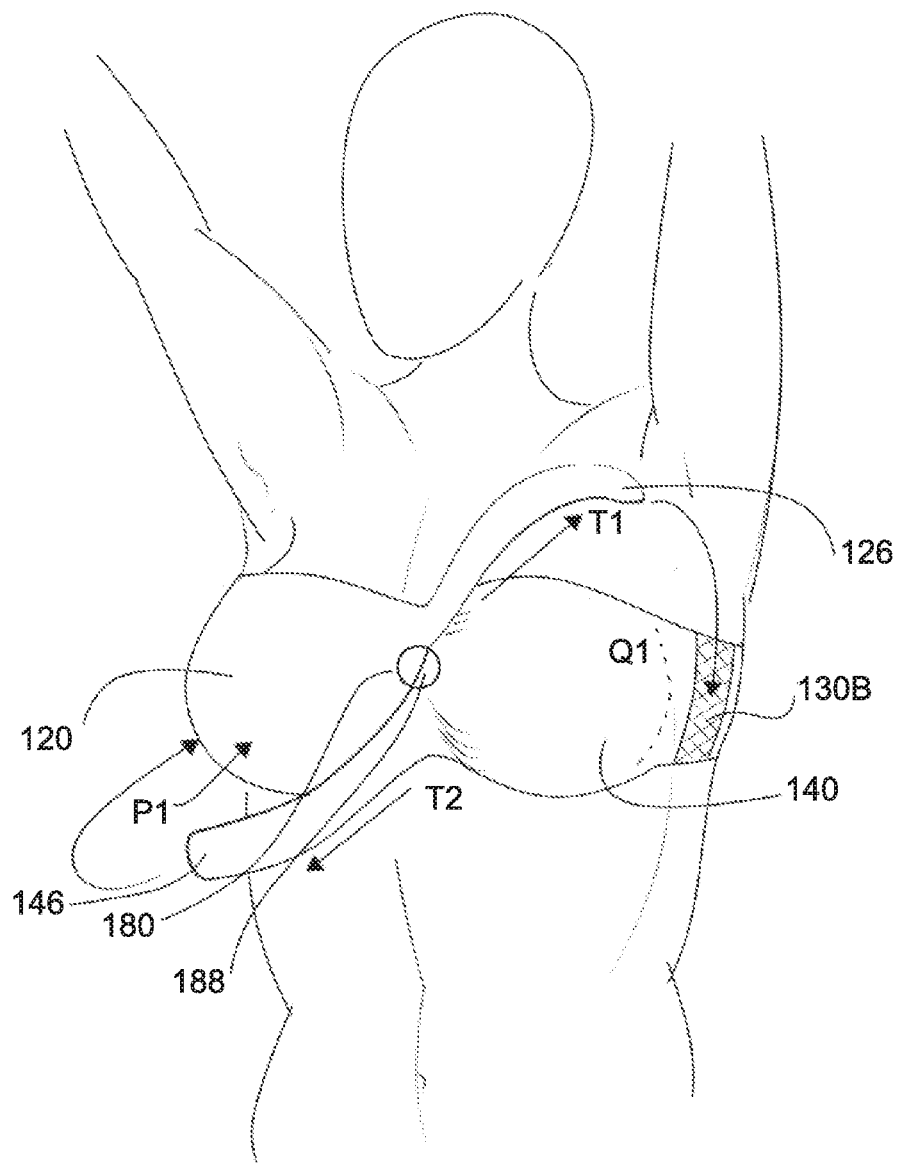
FIG. 7 illustrates in isometric view the example of FIG. 6 being secured to the torso of FIG. 3.

Referring to FIG. 7, the chest support 100 is caused to encircle the torso E by bringing the first breast support 120 into proximity with the second breast support 140 over the sternum, and then the two are engaged via the first auxiliary fastener 180. The second auxiliary fastener 188 can also be engaged. In this position, the chest support 100 is held in light abutment with the torso for general alignment therewith, though not particularly tightly abutted.

Figure 8:
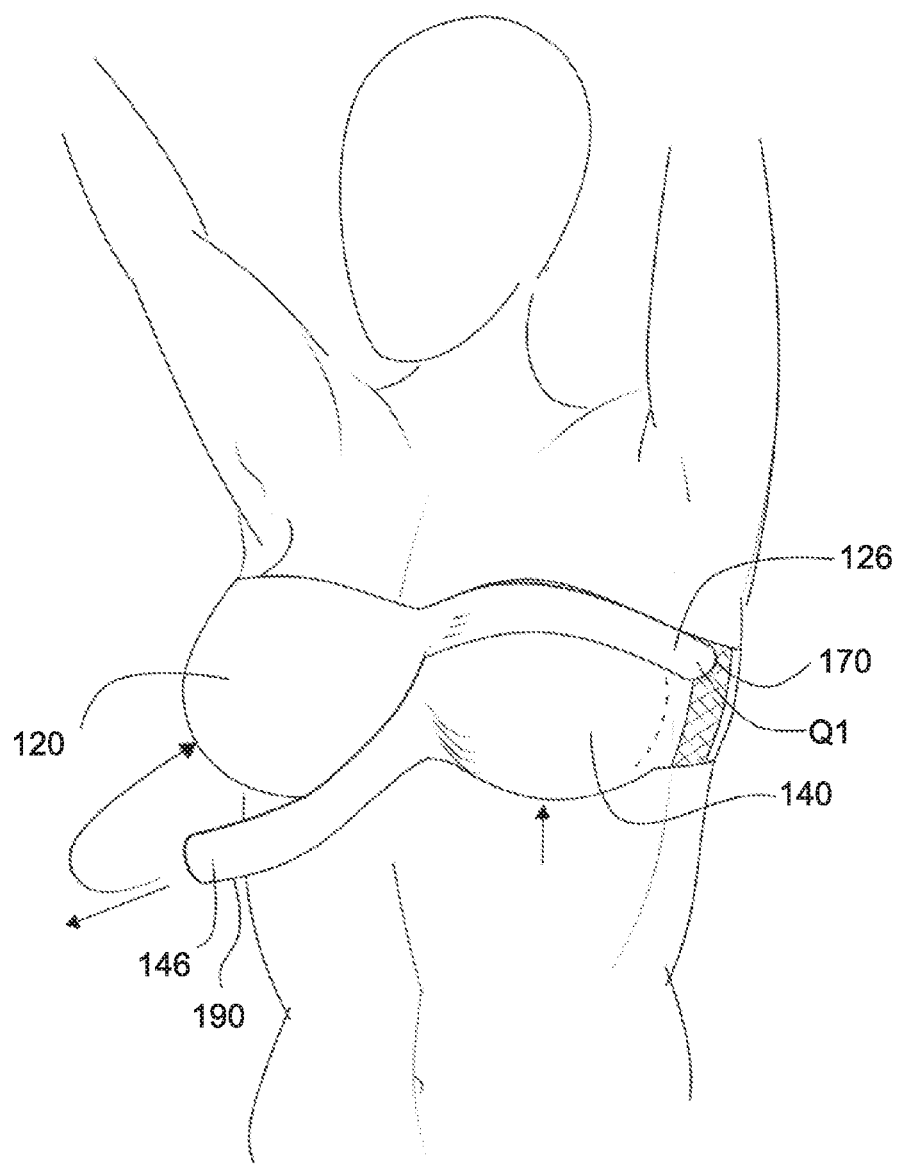
FIG. 8 illustrates in isometric view the example of FIGS. 6 and 7 partially affixed/donned to the torso of FIG. 3.

Referring to FIG. 7 again and to FIG. 8, the free first outer lateral end 126 in particular first tongue 125 is now pulled in a general lateral direction towards the second breast support 140, inducing a tension T1 at least in the free first outer lateral end 126 while this is resisted at abutment zone AZ by the second breast support 140. In turn, this tension T1 generates a desired supporting pressure P1 on the first breast area A via the first breast support 120, in particular the resilient first breast receiving panel 122, and thereafter the first outer lateral end 126 in particular first tongue 125 is affixed onto the second breast support 140 via the first fastener 170 at the corresponding position Q1, thereby maintaining tension T1 and support pressure P1 on the first breast area A. Thus, a portion of the first breast support 120, in particular at least a portion of the free first outer lateral end 126, and more in particular a portion of first tongue 125, is in overlapping abutting relationship with a corresponding portion of the second breast support 140.

Referring again to FIG. 4, the free second outer lateral end 146 in particular second tongue 145 is now pulled in a general lateral direction towards the first breast support 120, inducing a tension T2 at least in the free second outer lateral end 146, while this is resisted at abutment zone AZ by the first breast support 120. In turn, this tension T2 generates a desired supporting pressure P2 on the second breast area B via the second breast support 140, in particular the resilient second breast receiving panel 142, and thereafter the second outer lateral end 146 in particular second tongue 145 is affixed onto the first breast support 120 via the second fastener 190 at the corresponding position Q2, thereby maintaining tension T2 and support pressure P2 on the second breast area B. Thus, a portion of the second breast support 140, in particular at least a portion of the free second outer lateral end 146, and more in particular a portion of second tongue 145, is in overlapping abutting relationship with a corresponding portion of the first breast support 120.

Optionally, it is possible to reverse the order between FIG. 8 and FIG. 4, and thus first affix the free second outer lateral end 146, in particular second tongue 145, on the first breast support 120, and then affix the free first outer lateral end 126, in particular first tongue 125, on the second breast support 140.

In any case it is evident that in at least the above examples, the support pressure P1 that can be applied to the first breast area A by the first breast support 120 and first fastener 170 can be set to a desired value independently of the support pressure P2 that can be applied to the second breast area B by the second breast support 140 and second fastener 190.

The chest support 100 can be doffed or otherwise removed from the torso E, for example by reversing the donning operation as disclosed above.

Figure 10A:
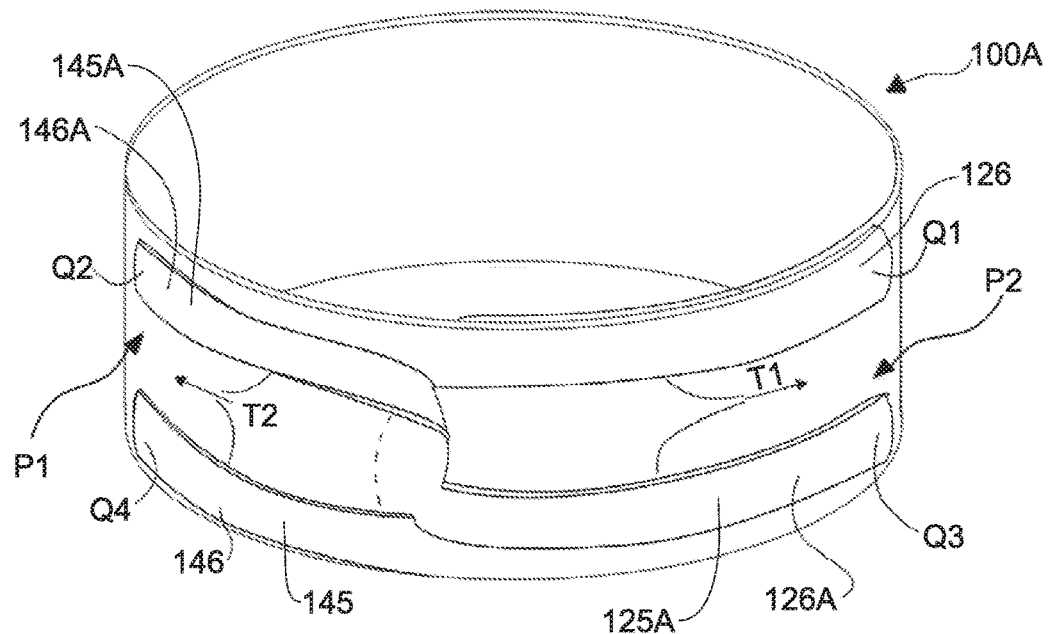
FIG. 10(a) shows in isometric front view another alternative variation of the example of FIG. 1, in affixed, donned configuration.
Figure 10B:
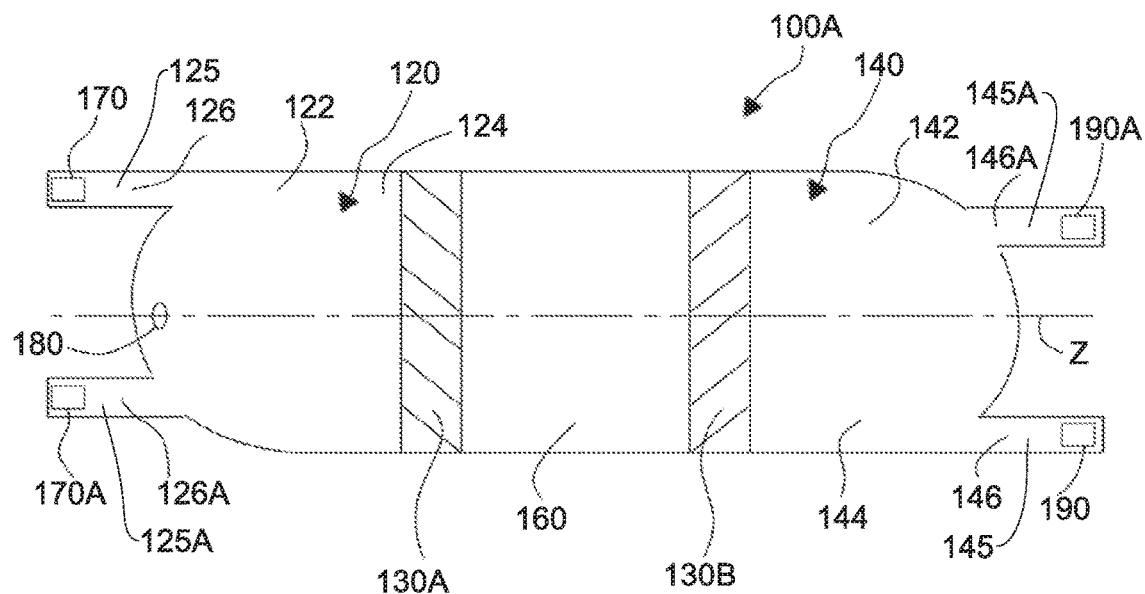
FIG. 10(b) shows in front view the example of FIG. 10(a), in laid-out, doffed configuration.

An alternative variation of the example illustrated in FIGS. 1 to 9(b) is illustrated in FIGS. 10(a) and 10(b). The corresponding body or chest support, designated with the reference numeral 100A, is similar in form and function to the chest support 100 including other alternative variations thereof, as disclosed above, mutatis mutandis, with some differences, as will become clearer herein. Thus, chest support 100A comprises a plurality of structural elements including: first breast support 120 (including a resilient first breast receiving panel 122, and a first inner lateral end 124 and a free first outer lateral end 126 including first tongue 125), a second breast support 140 (including a resilient second breast receiving panel 142, and a second inner lateral end 144 and a free second outer lateral end 146 including second tongue 145), a connecting section 160, a first fastener 170 and a second fastener 190; optionally a first auxiliary fastener 180 and a/or a second auxiliary fastener 188; optionally stabilizing panels 130A, 130B; similar to the corresponding elements as disclosed for the embodiment of FIGS. 1 to 9(b), mutatis mutandis. Chest support 100A differs from chest support 100 mainly in that chest support 100A further comprises: a free third outer lateral end 126A including third tongue 125A, a third fastener 170A, a free fourth outer lateral end 146A including fourth tongue 145A, and a fourth fastener 190A.

The third outer lateral end 126A including third tongue 125A is similar to the free first outer lateral end 126 including first tongue 125, mutatis mutandis, but s located on an in inferior part of the first breast support 120, and includes at least a part of the third fastener 170A. The third fastener 170A is similar in form and function as disclosed herein for the first fastener 170, mutatis mutandis.

The fourth outer lateral end 146A including fourth tongue 145A is similar to the free second outer lateral end 146 including second tongue 145, mutatis mutandis, but is located on a superior part of the second breast support 140, and includes at least a part of the fourth fastener 190A. The fourth fastener 190A is similar in form and function as disclosed herein for the second fastener 190, mutatis mutandis.

As best seen in FIG. 10(b), the free first outer lateral end 126 (including first tongue 125) and the third outer lateral end 126A (including third tongue 125A) are not symmetrically disposed with respect to one another on different sides of axis Z, and similarly, the free second outer lateral end 146 (including second tongue 145) and the fourth outer lateral end 146A (including fourth tongue 145A) are also asymmetrically disposed with respect to one another on different sides of axis Z.

Thus, while the free first outer lateral end 126 (including first tongue 125) is spaced further from the axis Z than the fourth outer lateral end 146A (including fourth tongue 145A), the free second outer lateral end 146 (including second tongue 145) is now spaced further from the axis Z than the third outer lateral end 126A (including third tongue 125A).

Operation of chest support 100A, i.e. donning and/or doffing the chest support 100A, is similar to that of chest support 100, mutatis mutandis, the main differences being as follows. In this example tension T2 can be applied on the second breast area B via the second breast support 140 by suitably pulling each of the free second outer lateral end 146 (in particular second tongue 145) and the fourth outer lateral end 146A (in particular fourth tongue 145A), independently of one another, over the first breast support 120, and securing the free second outer lateral end 146 (in particular second tongue 145) and the fourth outer lateral end 146A (in particular fourth tongue 145A) to the first breast support 120 at positions Q2 and Q4, respectively. In this example tension T1 can similarly be applied on the first breast area A via the first breast support 120 by suitably pulling each of the free first outer lateral end 126 (in particular second tongue 125) and the third outer lateral end 126A (in particular third tongue 145A), independently of one another, over the second breast support 140, and securing the free first outer lateral end 126 (in particular first tongue 125) and the third outer lateral end 126A (in particular third tongue 125A) to the second breast support 140 at positions Q1 and Q3, respectively.

It is to be noted that each of the respective first tensions T1 provided by pulling the free first outer lateral end 126 (in particular first tongue 125) and the third outer lateral end 126A (in particular third tongue 125A), can be the same or different. For example, the first outer lateral end 126 (in particular first tongue 125) can be pulled to apply a large tension T1, while third outer lateral end 126A (in particular third tongue 125A) is only pulled sufficiently to be taut, and thus the first pressure P1 is provided almost entirely via the first outer lateral end 126 (in particular first tongue 125). Similarly, each of the respective second tensions T2 provided by pulling free second outer lateral end 146 (in particular second tongue 145) and the fourth outer lateral end 146A (in particular fourth tongue 145A), can be the same or different. For example, the free second outer lateral end 146 (in particular second tongue 145) can be pulled to apply a large tension T2, while free first outer lateral end 126 (in particular first tongue 125) is only pulled sufficiently to be taut, and thus the second pressure P2 is provided almost entirely via the second outer lateral end 146 (in particular second tongue 145).

Thus, one or both of the first outer lateral end 126 (in particular first tongue 125) and the fourth outer lateral end 146A (in particular fourth tongue 145A) support the chest C at a respective superior location, while one or both of the second outer lateral end 146 (in particular second tongue 145) and the third outer lateral end 126A (in particular third tongue 125A) support the chest C at a respective inferior location.

It is readily evident that a portion of the second breast support 140, in particular at least a portion of the free second outer lateral end 146 (in particular a portion of second tongue 145) and a portion of the free fourth outer lateral end 146A (in particular a portion of fourth tongue 145A), are each in overlapping abutting relationship with a respective portion of the first breast support 120. It is also readily evident that a portion of the first breast support 120, in particular at least a portion of the free first outer lateral end 126 (in particular a portion of first tongue 125) and a portion of the free third outer lateral end 126A (in particular a portion of third tongue 125A), are each in overlapping abutting relationship with a respective portion of the second breast support 140.

Figure 11A:
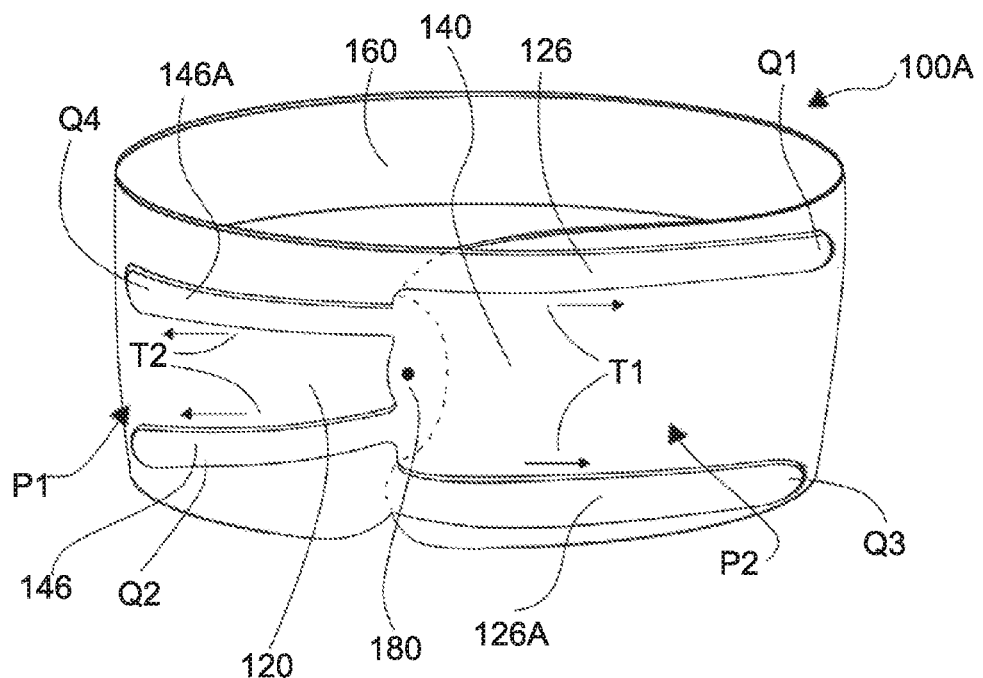
FIG. 11(a) shows in isometric front view an alternative variation of the example of FIGS. 10(a) and 10(b), in affixed, donned configuration.
Figure 11B:
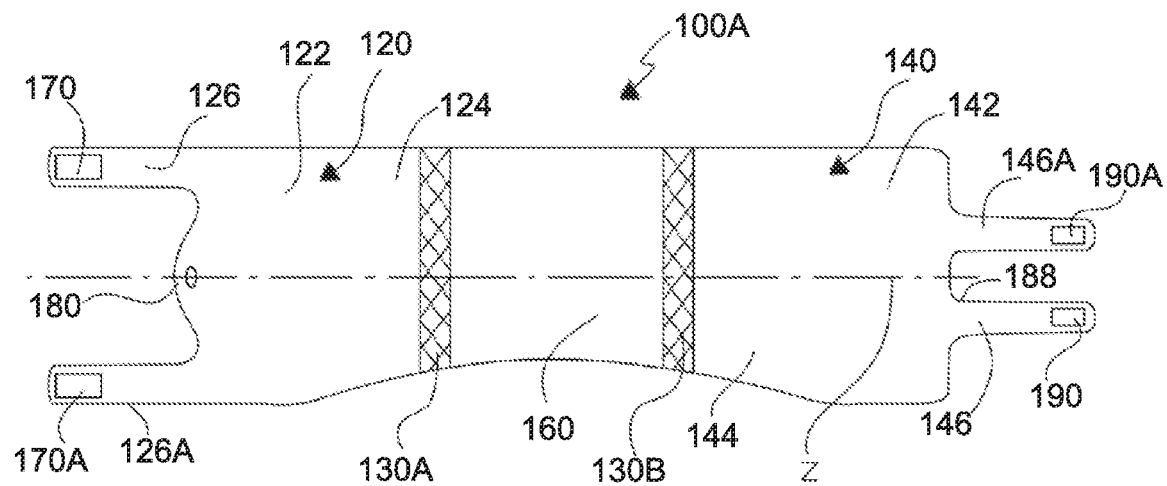
FIG. 11(b) shows in front view the example of FIG. 11(a), in laid-out, doffed configuration.

Referring to FIGS. 11(a) and 11(b), in an alternative variation of the example of FIGS. 10(a) and 10(b), the free first outer lateral end 126 (in particular first tongue 125) and the third outer lateral end 126A (in particular third tongue 125A) are symmetrically disposed with respect to one another on different sides of axis Z, and similarly, the free second outer lateral end 146 (in particular second tongue 145) and the fourth outer lateral end 146A (in particular fourth tongue 145A) are also symmetrically disposed with respect to one another on different sides of axis Z.

Thus, the free first outer lateral end 126 (in particular first tongue 125) is spaced further from the axis Z than the fourth outer lateral end 146A (in particular fourth tongue 145A), and the third outer lateral end 126A (in particular third tongue 125A) is spaced further from the axis Z than the free second outer lateral end 146 (in particular second tongue 145).

Thus, when donned, in the example of FIGS. 10(a) and 10(b) the free second outer lateral end 146 (in particular first tongue 125) is located at an inferior position with respect to the third outer lateral end 126A (in particular third tongue 125A), while in the example of FIGS. 11(a) and 11(b), the free second outer lateral end 146 (in particular second tongue 145) is located at a superior position with respect to the third outer lateral end 126A (in particular fourth tongue 145A). It is to be noted that for both examples illustrated in FIGS. 10(a), 10(b), 11(a) and 11(b), when donned, the first outer lateral end 126 (in particular first tongue 125) is located at a superior position with respect to fourth outer lateral end 146A (in particular fourth tongue 145A).

Figure 12A:
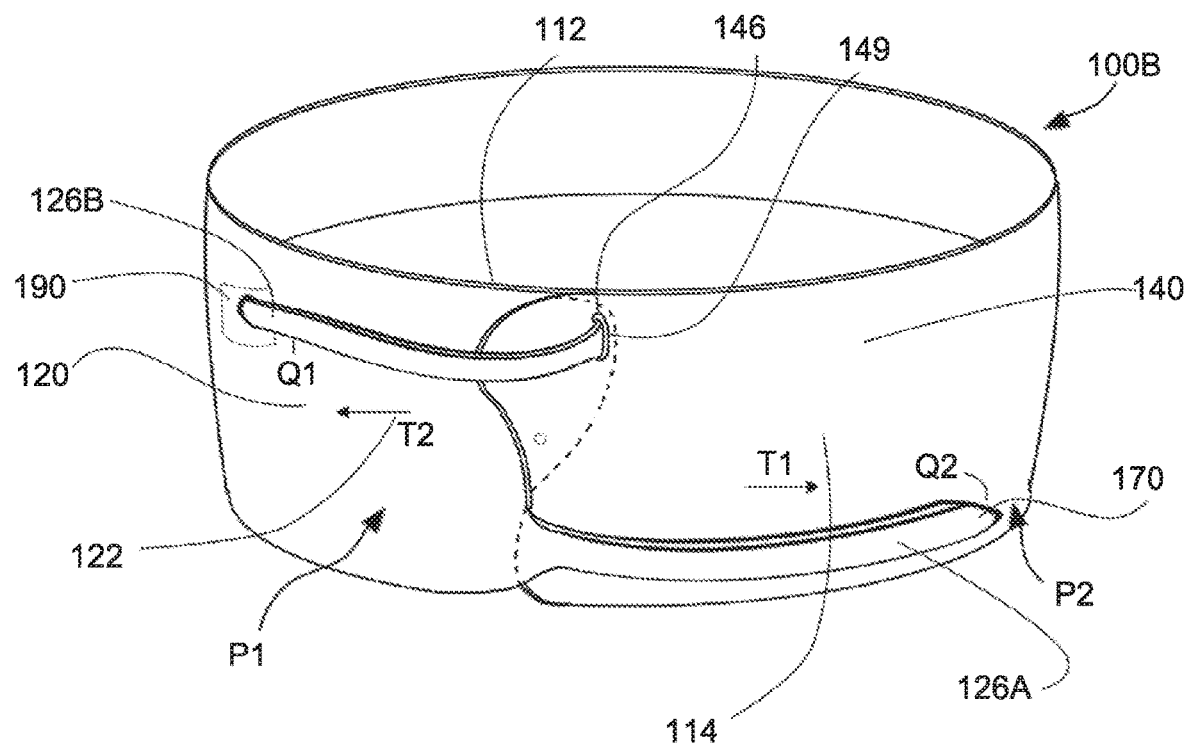
FIG. 12(a) shows in isometric front view another alternative variation of the example of FIG. 1, in affixed, donned configuration.
Figure 12B:
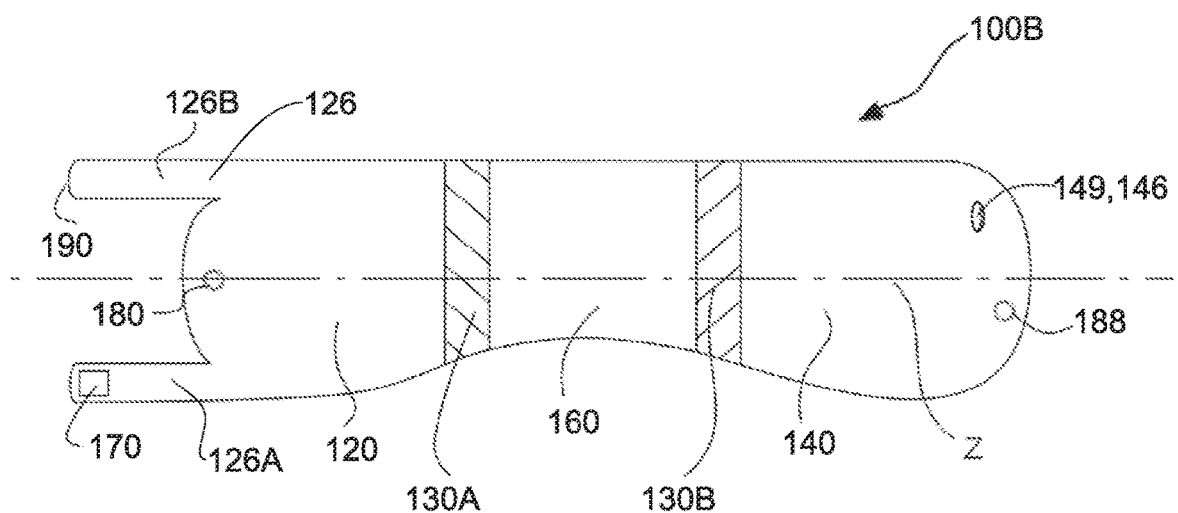
FIG. 12(b) shows in front view the example of FIG. 12(a), in laid-out, doffed configuration.

An alternative variation of the example illustrated in FIGS. 1 to 9(b) is illustrated in FIGS. 12(a) and 12(b). The corresponding body or chest support, designated with the reference numeral 100B, is similar in form and function to the chest support 100 disclosed above including other alternative variations thereof, as disclosed above, mutatis mutandis, with some differences, as will become clearer herein. Thus, chest support 100B comprises a plurality of structural elements including: first breast support 120 (including a resilient first breast receiving panel 122, and a first inner lateral end 124 and a free first outer lateral end 126 (including first tongue 126A)), a second breast support 140 (including a resilient second breast receiving panel 142, and a second inner lateral end 144 and a free second outer lateral end 146), a connecting section 160, a first fastener 170 and a second fastener 190; optionally a first auxiliary fastener 180 and a/or a second auxiliary fastener 188; optionally stabilizing panels 130A, 130B; similar to the corresponding elements as disclosed for the example of FIGS. 1 to 9(b), mutatis mutandis, but with some differences as disclosed below.

Chest support 100B differs from chest support 100 or chest support 100A mainly in that the free second outer lateral end 146 includes an opening 149 laterally offset from the lateral edge of the second breast support 140. The opening 149 allows a first auxiliary tongue 126B (laterally projecting from a superior location of the first breast support 120 (e.g. similar to free first outer lateral end 126, mutatis mutandis)) to be looped therethrough, from the inner facing side 122 to the outer facing side 114, and laterally back towards the first breast support 120 on an outer facing side thereof. At least a portion of the second fastener 190 is provided on the first auxiliary tongue 126B and the first breast support 120 to allow the first auxiliary tongue 126B to be laterally pulled over the first breast support 120 and secured to any one of a number of different locations Q1', thereby applying tensile load T2 to putt the second breast support 140 and in particular the resilient second breast receiving panel 142, to thereby apply the support pressure P2 over the second breast area B. Alternatively the opening 149 can be replaced with a loop, ring, hoop or the like provided at or in proximity to lateral edge of the second breast support 140.

Furthermore, in the example of FIGS. 12(a) and 12(b), the first outer lateral end 126 (via first tongue 126A) supports the chest C at a respective inferior location, while the second outer lateral end 146 (via first auxiliary tongue 126B) supports the chest C at a respective superior location. Thus in this example, the first outer lateral end 126, in particular first tongue 126A projects laterally from the first breast support 120 at an inferior location. However, in alternative variations of the example of FIGS. 12(a) and 12(b), the chest support 100B is configured such that the first outer lateral end 126 supports the chest C at a respective superior location, while the second outer lateral end 146 (via first auxiliary tongue 126B) supports the chest C at a respective inferior location.

As best seen in FIG. 12(b), the free first outer lateral end 126 (in particular first tongue 126A) and the first auxiliary tongue 126B are symmetrically disposed with respect to one another on different sides of axis Z, and the free first outer lateral end 126 and the first auxiliary tongue 126B are of similar shape and size. However, in alternative variations of this example, the free first outer lateral end 126 (in particular first tongue 126A) and the first auxiliary tongue 126B are asymmetrically disposed with respect to one another on different sides of axis Z, and/or the free first outer lateral end 126 (in particular first tongue 126A) and the first auxiliary tongue 126B are of not similar in shape and/or in size to one another.

Operation of chest support 100B, i.e. donning and/or doffing the chest support 100A, is similar to that of chest support 100, mutatis mutandis, the main differences being as follows. In this example tension T2 can be applied on the second breast area B via the second breast support 140 by suitably pulling the second outer lateral end 146 (via first auxiliary tongue 126B when looped through opening 149) over the first breast support 120, and securing the first auxiliary tongue 126B to the first breast support 120 at position Q1'. In this example tension T1 can be applied on the first breast area A via the first breast support 120 as disclosed for the example of FIGS. 1 to 9(b).

It is readily evident that in chest support 100B, a portion of the second breast support 140, in particular at least a portion of the free second outer lateral end 146 is in overlapping abutting relationship with a respective portion of the first breast support 120. It is also readily evident that a portion of the first breast support 120, in particular at least a portion of the free first outer lateral end 126 (in particular a portion of first tongue 126A) is in overlapping abutting relationship with a respective portion of the second breast support 140.

Figure 13A:
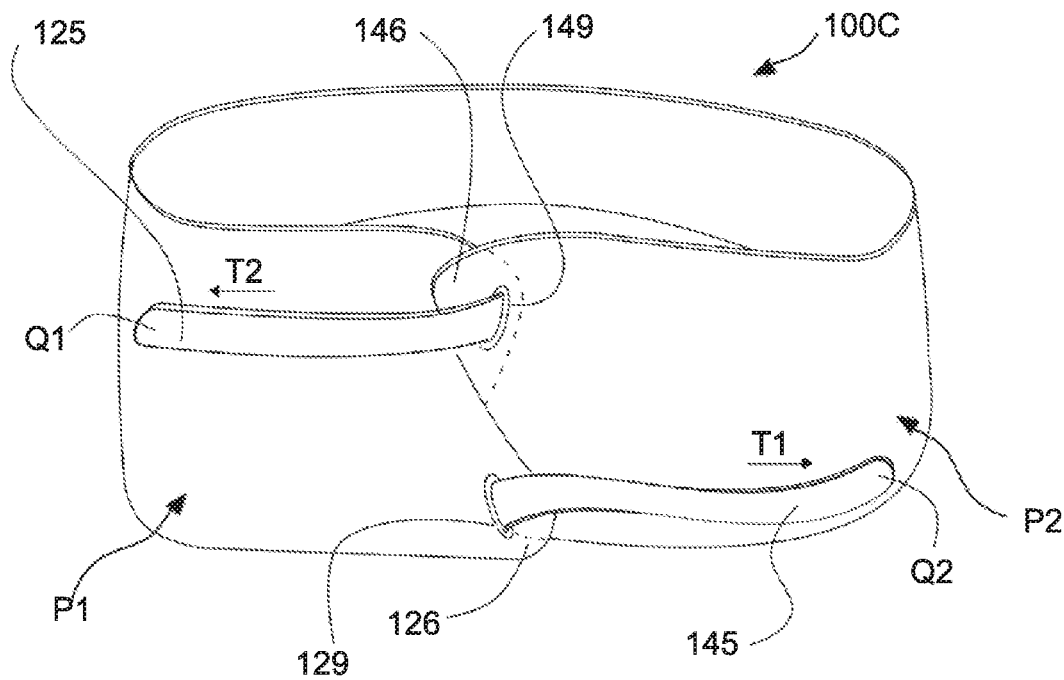
FIG. 13(a) shows in isometric front view another alternative variation of the example of FIG. 1, in affixed, donned configuration.
Figure 13B:
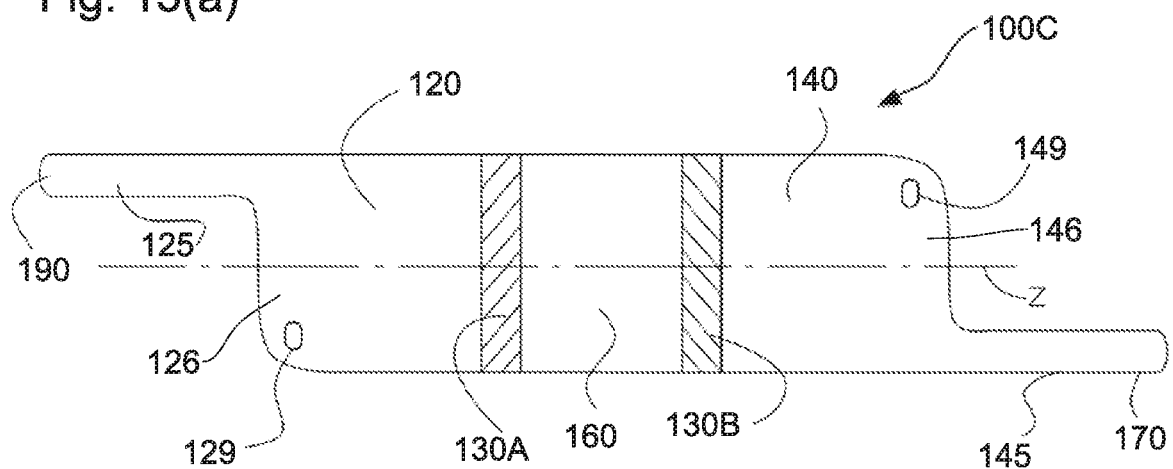
FIG. 13(b) shows in front view the example of FIG. 13(a), in laid-out, doffed configuration.

Another alternative variation of the example illustrated in FIGS. 1 to 12(b) is illustrated in FIGS. 13(a) and 13(b). The corresponding body or chest support, designated with the reference numeral 100C, is similar in form and function to the chest support 100 disclosed above including other alternative variations thereof, in particular chest support 100B, as disclosed above, mutatis mutandis, with some differences, as will become clearer herein. Thus, chest support 100C comprises a plurality of structural elements including: first breast support 120 (including a resilient first breast receiving panel 122, and a first inner lateral end 124 and a free first outer lateral end 126 (including first tongue 125)), a second breast support 140 (including a resilient second breast receiving panel 142, and a second inner lateral end 144 and a free second outer lateral end 146 (including second tongue 145)), a connecting section 160, a first fastener 170 and a second fastener 190; optionally a first auxiliary fastener 180 and a/or a second auxiliary fastener 188; optionally stabilizing panels 130A, 130B; similar to the corresponding elements as disclosed for the example of FIGS. 1 to 9(b), mutatis mutandis, but with some differences as disclosed below.

Chest support 100C differs from chest support 100 mainly in that the free second outer lateral end 146 includes an opening 149 laterally offset from the lateral edge of the second breast support 140, in a similar manner to the example of FIGS. 12(a) and 12(b), mutatis mutandis. Thus, the opening 149 allows a first tongue 126 projecting from the first breast support 120 (e.g. similar to free first outer lateral end 126) to be looped therethrough, from the inner facing side 122 to the outer facing side 114, and laterally back towards the first breast support 120 on an outer facing sided thereof. At least a portion of the second fastener 190 is provided on the first tongue 125 and the first breast support 120 to allow the second outer lateral end 146 (via first tongue 125 when looped through opening 149) to be laterally pulled over the first breast support 120 and affixed to any one of a number of different locations Q1', thereby applying tensile load T2 to pull the second breast support 140 and in particular the resilient second breast receiving panel 142, to thereby apply the support pressure P2 over the second breast area B. Alternatively the opening 149 can be replaced with a loop, ring, hoop or the like provided at or in proximity to lateral edge of the second breast support 140.

Chest support 100C differs from chest support 100 or chest support 100B further in that the free first outer lateral end 126 includes an opening 129 laterally offset from the lateral edge of the first breast support 120. The opening 129 allows a second tongue 145 projecting from the second breast support 140 (e.g. similar to the first tongue 125) to be looped therethrough, from the inner facing side 122 to the outer facing side 114, and laterally back towards the second breast support 140. At least a portion of the first fastener 170 is provided on the second tongue 145 and the second breast support 140 to allow the first outer lateral end 126 (via second tongue 145 when lopped through opening 129) to be laterally pulled over the second breast support 140 and secured to any one of a number of different locations Q2', thereby applying tensile load T1 to pull the first breast support 120 and in particular the resilient first breast receiving panel 122, to thereby apply the support pressure P1 over the first breast area A. Alternatively the opening 129 can be replaced with a loop, ring, hoop or the like provided, at or in proximity to lateral edge of the first breast support 120.

In the example of FIGS. 13(a) and 13(b), the first outer lateral end 126 (via second tongue 145) supports the chest C at a respective inferior location, while the second outer lateral end 146 (via first tongue 125) supports the chest C at a respective superior location. However, in alternative variations of the example of FIGS. 13(a) and 13(b), the chest support 100C is configured such that the first outer lateral end 126 (via second tongue 145) supports the chest C at a respective superior location, while the second outer lateral end 146 (via first tongue 125) supports the chest C at a respective inferior location.

As best seen in FIG. 13(b), the first tongue 125 and the second tongue 145 are asymmetrically disposed with respect to one another on different sides of axis Z, and the first tongue 125 and the second tongue 145 are of similar shape and size. However, in alternative variations of this example, the first tongue 125 and the second tongue 145 are of not similar in shape and/or in size to one another.

Operation of chest support 100C, i.e. donning and/or doffing the chest support 100C, is similar to that of chest support 100 and to that of chest support 100B, mutatis mutandis, the main differences being as follows. In this example tension T2 can be applied on the second breast area B via the second breast support 140 by suitably pulling the second outer lateral end 146 (via first tongue 125 when looped through opening 149) over the first breast support 120, and securing the first tongue 125 to the first breast support 120 at position Q1'. In this example tension T1 can similarly be applied on the first breast area A via the first breast support 120 by suitably pulling the first lateral end 126 (via second tongue 145 when looped through opening 129) over the second breast support 140, and securing the second tongue 145 to the second breast support 140 at position Q2'.

It is readily evident that in chest support 100C, a portion of the second breast support 140, in particular at least a portion of the free second outer lateral end 146 is in overlapping abutting relationship with a respective portion of the first breast support 120. It is also readily evident that a portion of the first breast support 120, in particular at least a portion of the free first outer lateral end 126 is in overlapping abutting relationship with a respective portion of the second breast support 140.

Figure 14A:
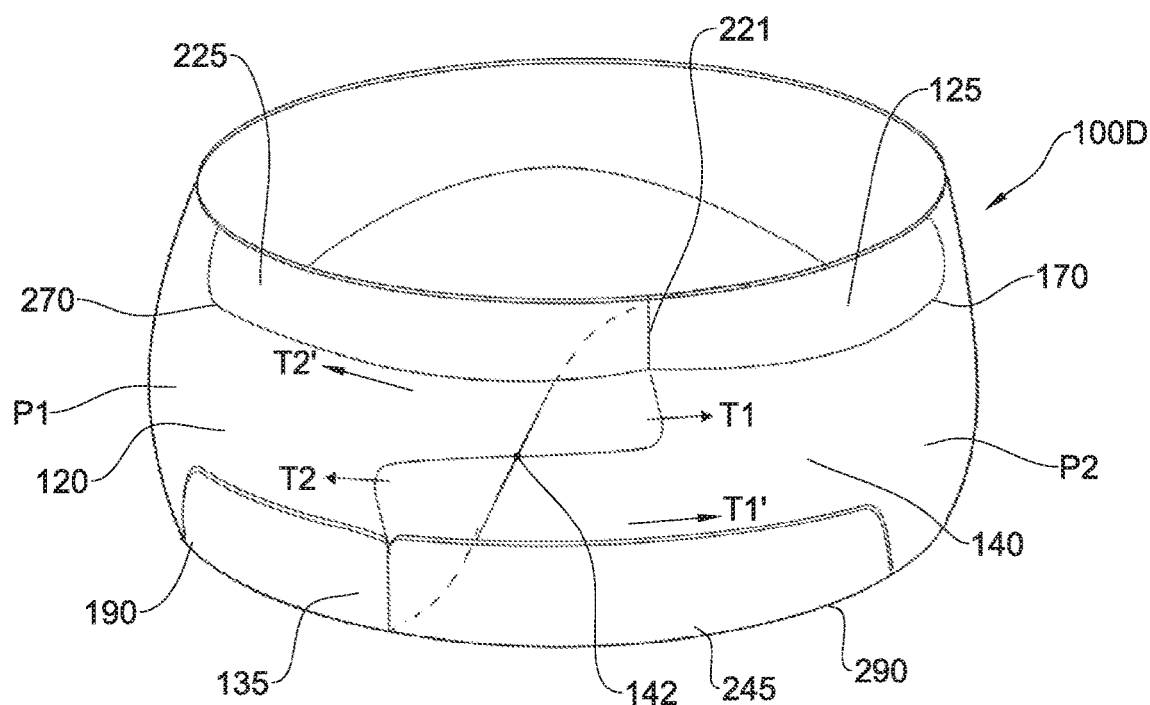
FIG. 14(a) shows in isometric front view another alternative variation of the example of FIG. 1, in affixed, donned configuration.
Figure 14B:
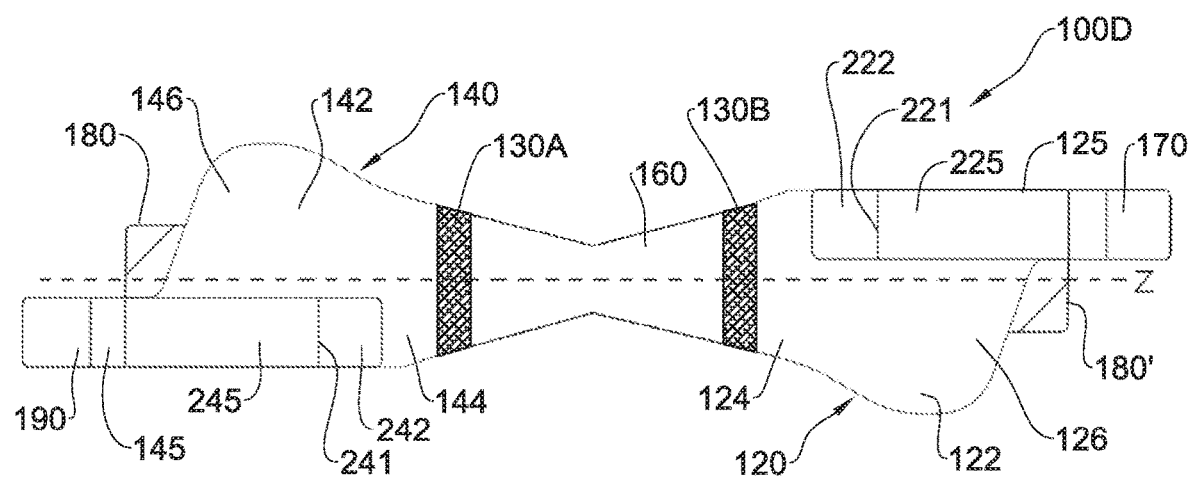
FIG. 14(b) shows in front view the example of FIG. 12(a), in laid-out, doffed configuration.

An alternative variation of the example illustrated in FIGS. 1 to 9(b) is illustrated in FIGS. 14(a) and 14(b). The corresponding body or chest support, designated with the reference numeral 100D, is similar in form and function to the chest support 100 including other alternative variations thereof, as disclosed above, mutatis mutandis, with some differences, as will become clearer herein. Thus, chest support 100D comprises a plurality of structural elements including: first breast support 120 (including a resilient first breast receiving panel 122, and a first inner lateral end 124 and a free first outer lateral end 126 including first tongue 125), a second breast support 140 (including a resilient second breast receiving panel 142, and a second inner lateral end 144 and a free second outer lateral end 146 including second tongue 145), a connecting section 160, a first fastener 170 and a second fastener 190; optionally a first auxiliary fastener 180; optionally stabilizing panels 130A, 130B; similar to the corresponding elements as disclosed for the embodiment of FIGS. 1 to 9(b), mutatis mutandis.

Chest support 100D differs from chest support 100 mainly in that chest support 100D further comprises: a first auxiliary tongue 225 and a second auxiliary tongue 245. Optionally, Chest support 100D can further comprise an additional first auxiliary fastener 180', for example similar to (and additional to or instead of) first auxiliary fastener 180 but provided at the other breast support.

The first auxiliary tongue 225 projects from said first outer lateral end and comprises a first auxiliary fastener 270 configured for selectively and reversibly affixing the first auxiliary tongue 225 with respect to the first breast support 120 at least at one first location, in the donned configuration, such that a portion of the first auxiliary tongue 225 is in overlapping abutting relationship with a respective portion of the first breast support. Accordingly, an additional tensile load T2' is induced, wherein to enhance said first support pressure P1.

The first auxiliary tongue 225 in this example is connected at one longitudinal end 221 thereof to an inner end 222 of the first tongue 125. At least prior to donning the body support 100D, and referring to FIG. 14(b) in particular, the first auxiliary tongue 225 is in overlying relationship with the first tongue 125. After affixing the first tongue 125 to the second support 140, the first auxiliary tongue 225 is pivoted about end 221 thereof away from the first tongue 125 to enable the first auxiliary tongue 225 to be affixed with respect to said first support 120, as illustrated in FIG. 14(a).

The second auxiliary tongue 245 projects from said second outer lateral end and comprises a second auxiliary fastener 290 configured for selectively and reversibly affixing the second auxiliary tongue 245 with respect to the second breast support 140 at least at one second location, in the donned configuration, such that a portion of the second auxiliary tongue 245 is in overlapping abutting relationship with a respective portion of the second breast support. Accordingly, an additional tensile load T1' is induced, wherein to enhance said second support pressure P2.

The second auxiliary tongue 245 in this example is connected at one longitudinal end 241 thereof to an inner end 242 of the second tongue 145. At least prior to donning the body support 100D, and referring to FIG. 14(b) in particular, the second auxiliary tongue 245 is in overlying relationship with the second tongue 145. After affixing the second tongue 145 to the first support 120, the second auxiliary tongue 245 is pivoted about end 241 thereof away from the second tongue 145 to enable the second auxiliary tongue 245 to be affixed with respect to said second support 140, as illustrated in FIG. 14(a).

Thus, operation of chest support 100D, i.e. donning and/or doffing the chest support 100D, is similar to that of chest support 100, mutates mutandis, the main differences being the additional tensile loads provided by the first auxiliary tongue 225 and the second auxiliary tongue 245. It is to be noted that these tensile loads T1' and T2' can be independently varied, in a similar manner to the manner in which tensile loads T1 or T2 can be varied, mutatis mutandis, thereby providing additional control over the support pressures P1 and P2.

It is to be noted that in alternative variations of this example one or the other of the first auxiliary tongue 225 and the second auxiliary tongue 245 can be omitted.

The chest support 100D can be made in a similar manner to that disclosed herein in relation to FIGS. 5(a) to 5(f), with the additional step of including the first auxiliary tongue 225 and the second auxiliary tongue 245 in the manufacturing process. For example, the first auxiliary tongue 225 and the second auxiliary tongue 245 can be stitched onto the chest support at longitudinal end 221 and longitudinal end 241, respectively. Alternatively, the first auxiliary tongue 225 is formed integrally with the first tongue 125, and folded at longitudinal end 221, and then the first tongue 125 is fixed onto the chest support; similarly the second auxiliary tongue 245 is formed integrally with the second tongue 145, and folded at longitudinal end 241, and then the second tongue 145 is fixed onto the chest support.

It is to be noted that in alternative variations of this example the corresponding body or chest support can have a plurality of such first auxiliary tongue 225 and/or a plurality of such second auxiliary tongue 245, optionally with a plurality of first tongues 125 and/or a plurality of second tongues 145.

It is also to be noted that in alternative variations of other examples illustrated herein that include at least a first tongue and/or a second tongue at least one first auxiliary tongue 225 can be provided thereto, and/or at least one second auxiliary tongue 245 can be provided thereto.

It will be appreciated that in variations of the above examples, the chest support can be configured mutatis mutandis, as a body support for covering and supporting other body portions of human beings or of animals, comprising, inter alia, for example any one of: an arm, a palm, a finger, a leg, a foot, a toe, an abdomen, a hip, a neck. In such cases, the respective body support is suitably dimensioned to enable encircling and affixing to the respective body support.

Finally, it should be noted that the word "comprising" as used throughout the appended claims is to be interpreted to mean "including but not limited to".

While there has been shown and disclosed examples in accordance with the presently disclosed subject matter, it will be appreciated that many changes can be made therein without departing from the spirit of the presently disclosed subject matter.

The invention claimed is:

1. A body support for covering and supporting at least a first body area and a second body area of a body portion, each one of the first body area and the second body area being on a different lateral side of a median plane of the body portion, the body support having a donned configuration and a doffed configuration with respect to the body portion, the body support comprising:
   a first support comprising a resilient first panel, a first inner lateral end and a first outer lateral end, wherein said first outer lateral end is free and spaced from said first inner lateral end;
   a second support comprising a resilient second panel, a second inner lateral end and a second outer lateral end, wherein said second outer lateral end is free and spaced from said second inner lateral end;
   a connecting section joined to the first inner lateral end and to the second inner lateral end for thereby enabling, in the donned configuration, encircling and supporting the body portion when affixed thereto;
   at least one first tongue outwardly projecting from said first outer lateral end and comprising a first fastener configured for selectively and reversibly affixing said first support with respect to said second support at least at one first location, in the donned configuration, such that a portion of said first tongue is in overlapping abutting relationship with a respective portion of said second support, wherein to enable a first support pressure to be induced to the first body area by abutting contact therewith; and
   at least one second tongue outwardly projecting from said second outer lateral end and comprising a second fastener, different from said first fastener, configured for selectively and reversibly affixing said second support with respect to said first support at least at one second location, in the donned configuration, such that a portion of said second tongue is in overlapping abutting relationship with a respective portion of said first support, wherein to enable a second support pressure to be induced to the second body area by abutting contact therewith,
   wherein in the doffed configuration the first support and the second support are non-contiguous with respect to one another;
   and further including at least one of:
      (a) wherein the first support further comprises at least one first auxiliary tongue projecting from said first outer lateral end and comprising a first auxiliary fastener configured for selectively and reversibly affixing a respective said at least one first auxiliary tongue with respect to said first support at least at another one first location, in the donned configuration, such that a portion of said at least one first auxiliary tongue is in overlapping abutting relationship with a respective portion of said first support, wherein to enhance said first support pressure; and (b) wherein the second support further comprises at least one second auxiliary tongue projecting from said second outer lateral end and comprising a second auxiliary fastener configured for selectively and reversibly affixing a respective said at least one second auxiliary tongue with respect to said second support at least at another one second location, in the donned configuration, such that a portion of said at least one second auxiliary tongue is in overlapping abutting relationship with a respective portion of said second support, wherein to enhance said second support pressure.

2. The body support according to claim 1, wherein:

at said at least one first location, a portion of said first outer lateral end is in overlapping abutting relationship with a respective portion of said second support;

said first support pressure is configured to be induced to the first body area by applying a first tension to said first outer lateral end and said first tension is applied by laterally pulling the first outer lateral end over the second support;

the body support comprises a plurality of said at least one first locations, each having a different lateral spacing with respect to the second support, wherein affixing said first support with respect to said second support at each different said plurality of said at least one first locations enables the first support pressure to be correspondingly varied; and said first fastener is configured for reversibly affixing said at least one first tongue with respect to an outer facing side of the second support.

3. The body support according to claim 1, wherein:

said first outer lateral end comprises a plurality of said at least one first tongues, each said first tongue outwardly projecting from said first panel, and wherein said first fastener is configured for reversibly affixing each respective said plurality of at least one first tongues with respect to an outer facing side of the second support; and said second outer lateral end comprises a plurality of said at least one second tongues, each said second tongue outwardly projecting from said second panel, and wherein said second fastener is configured for reversibly affixing said plurality of at least one second tongues with respect to an outer facing side of the first support.

4. The body support according to claim 1, wherein:

said second outer lateral end comprises at least one first opening allowing a respective said at least one first tongue to be looped therethrough and in overlapping relationship with the first panel, and wherein said second fastener is configured for reversibly affixing the respective said at least one first tongue with respect to an outer facing side of the first support; and said first outer lateral end comprises at least one second opening allowing a respective said at least one second tongue to be looped therethrough and in overlapping relationship with the second panel, and wherein said first fastener is configured for reversibly affixing the respective said at least one second tongue with respect to an outer facing side of the second support.

5. The body support according to claim 1, wherein:

at said at least one second location, a portion of said second outer lateral end is in overlapping abutting relationship with a respective portion of said first support;

said second support pressure is configured to be induced to the second body area by applying a second tension to said second outer lateral end;

said second support pressure is configured to be induced to the second body area by applying a second tension to said second outer lateral end, and, wherein said second tension is applied by laterally pulling the second outer lateral end over the first support;

the body support comprises a plurality of said at least one second locations, each having a different lateral spacing with respect to the first support, wherein affixing said second support with respect to said first support at each different said at least one second locations enables the first support pressure to be correspondingly varied; and said second fastener is configured for reversibly affixing said at least one second tongue with respect to an outer facing side of the first support.

6. The body support according to claim 1, wherein said second support pressure is configured to be induced to the second body area by applying a second tension to said second outer lateral end, and:

either said first tension is applied laterally at a relatively superior position and said second tension is applied laterally at a relatively inferior position, and said first tension is applied laterally at a relatively inferior position and said second tension is applied laterally at a relatively superior position.

7. The body support according to claim 1, wherein:

the connecting section is laterally joined to each one of the first inner lateral end and to the second inner lateral end; and said connecting section is joined to the first inner lateral end and to the second inner lateral end for thereby enabling encircling and supporting the body portion when affixed thereto in the donned configuration, such that said first panel is in overlying abutting relationship with the first body area and said second panel is in overlying abutting relationship with the second body area, and such that at least a portion of said connecting section is configured to be in overlying abutting relationship with a back of the body portion.

8. The body support according to claim 1, wherein:

the body support further comprises at least one auxiliary fastener, different from said first fastener and said second fastener, each said at least one auxiliary fastener configured for reversibly affixing together the first support and the second support at an anterior position with respect to the body portion; or the body support further comprises at least one auxiliary fastener, different from said first fastener and said second fastener, each said at least one auxiliary fastener configured for reversibly affixing together the first support and the second support at an anterior position with respect to the body portion, and, wherein at least one said auxiliary fastener is configured for reversibly affixing together the first support and the second support at a generally medial anterior position, generally configured to correspond to a median plane of the body portion.

9. The body support according to claim 8, particularly configured as chest support, wherein:
said body portion is a torso, said first body area is a first breast area and said second body area is a second breast area of a chest corresponding to the torso, each one of the first breast area and the second breast area being on a different lateral side of a midsagittal plane of the torso; and
said first panel is a first breast receiving panel, and said second panel is a second breast receiving panel.

10. The body support according to claim 1, further comprising a pair of stabilizing panels, positioned on the body support a first of said stabilizing panels overlying a first part of the first support and a first part of the connecting section, and a second of said stabilizing panels overlying a second part of the second support and a second part of the connecting section, wherein each said stabilizing panel is generally non-elastic, at least in a lateral direction.

11. The body support according to claim 1, wherein:
said connecting section joins said first support to said second support in longitudinal spaced relationship along an imaginary longitudinal mid-line of the body support; and
said at least one first tongue is transversely spaced from said mid-line on a first transverse side of said mid-line, and said at least one second tongue is transversely spaced from said mid-line on a second transverse side of said mid-line, wherein said first transverse side and said second transverse side are opposite transverse sides of the mid-line.

12. The body support according to claim 1, wherein:
the first support further comprises said at least one first auxiliary tongue, and, wherein each said first auxiliary tongue is connected at one end thereof to an inner end of a corresponding said at least one first tongue, wherein at least prior to donning the body support said at least one first auxiliary tongue is in overlying relationship with the corresponding said at least one first tongue, and wherein said at least one first auxiliary tongue is pivoted about said one end thereof away from the corresponding said at least one first tongue to enable said at least one first auxiliary tongue to be affixed with respect to said first support;
the second support further comprises said at least one second auxiliary tongue, and, wherein each said second auxiliary tongue is connected at one end thereof to an inner end of a corresponding said at least one second tongue, wherein at least prior to donning the body support said at least one second auxiliary tongue is in overlying relationship with the corresponding said at least one second tongue, and wherein said at least one second auxiliary tongue is pivoted about said one end thereof away from the corresponding said at least one second tongue to enable said at least one second auxiliary tongue to be affixed with respect to said second support.

13. The body support according to claim 1, wherein:
in the doffed configuration the first support and the second support are permanently joined to one another exclusively via said connecting section;
at least in doffed configuration said first outer lateral end and said second outer lateral end are unattached to one another;
at least in the doffed configuration said first support and said second support are unattached directly to one another;
in use of the body support when supporting the body portion, there is an absence of a permanent fixation between said first outer lateral end and said second outer lateral end;
in the donned configuration the body support is configured to be affixed to the body portion exclusively via said first support pressure and said second support pressure;
said first support pressure results in a tightening of the body support adaptively over the body portion, at the general location of the at least one first tongue, adaptively in a predominantly lateral direction with respect to the body portion; and
said second support pressure results in a tightening of the body support adaptively over the body portion, at the general location of the at least one second tongue, adaptively in a predominantly lateral direction with respect to the body portion.

14. The body support according to claim 1, wherein said at least one first tongue is in parallel transversely spaced relationship with respect to said at least one second tongue.

15. The body support according to claim 1, wherein in the donned configuration, a first edge of said first outer lateral end is in abutment with a second edge of said second outer lateral end.

16. The body support according to claim 1, wherein in the donned configuration, a first edge of said first outer lateral end is in abutment with a second edge of said second outer lateral end at an abutment zone in cross-over configuration, wherein to allow a first portion of said first outer lateral end to overlie a second portion of said second outer lateral end, while concurrently allowing a first portion of said second outer lateral end to overlie a second portion of said first outer lateral end.

17. The body support according to claim 1, wherein the body support is formed as any one of a disposable article and a multiple use article.

18. The body support according to claim 1, wherein:
the first fastener and the second fastener are configured for applying said first support pressure and said second support pressure, respectively, independently of one another; and
the first fastener and the second fastener are configured for applying said first support pressure different from said second support pressure.

19. The body support according to claim 1, wherein said body portion is selected from the group consisting of an arm, a palm, a finger, a leg, a foot, a toe, an abdomen, a hip and a neck.

20. The body support according to claim 1, wherein:
said body portion is a torso, said first body area is a first breast area and said second body area is a second breast area of a chest corresponding to the torso, each one of the first breast area and the second breast area being on a different lateral side of a midsagittal plane of the torso; and
said first panel is a first breast receiving panel configured to receive said first breast area of said chest, and said second panel is a second breast receiving panel configured to receive said second breast area of said chest.

21. The body support according to claim 20, wherein said at least one first tongue is transversely spaced with respect to said at least one second tongue by a transverse spacing, wherein said transverse spacing is generally not less than a height dimension of the first breast area or of the second breast area.

22. The body support according to claim 20, comprising a pair of stabilizing panels, positioned on the body support such as to be in overlying relationship with a respective one of a left side of an upper rib cage and a right side the upper rib cage, respectively, of the torso, when the body support is configured to encircle the torso and support the chest in the donned configuration, wherein each said stabilizing panel is generally non-elastic, at least in a lateral direction.

23. The body support according to claim 20, wherein:
said connecting section joins said first breast receiving panel to said second breast receiving panel in a longitudinal spaced relationship along a mid-line of the body support;
said at least one first tongue is transversely spaced from said mid-line on a first transverse side of said mid-line, and said at least one second tongue is transversely spaced from said mid-line on a second transverse side of said mid-line, wherein said first transverse side and said second transverse side are opposite transverse sides of the mid-line;
said first outer lateral end has a first edge obliquely crossing said mid-line, said first edge extending from said first breast receiving panel to said at least one first tongue;
said second outer lateral end has a second edge obliquely crossing said mid-line, said second edge extending from said second breast receiving panel to said at least one second tongue; and
in the donned configuration, said first edge of said first outer lateral end is in abutment with said second edge of said second outer lateral end.

24. A method of donning a body support on a body portion, comprising:
providing the body support as defined in claim 20;
encircling the torso with the body support such that first breast receiving panel is in overlying abutting relationship with the first breast area, the second breast receiving panel is in overlying abutting relationship with the second breast area, and the connecting section is in overlying abutting relationship with a back of the torso;
applying said first tension to the first breast receiving panel via the first outer lateral end, and affixing the first breast receiving panel with respect to the second support at a corresponding said at least one first location while maintaining said first tension, such as to induce said first support pressure to said first breast area; and
applying said second tension to the second breast receiving panel via the second outer lateral end, and affixing the second breast receiving panel with respect to the first support at a corresponding said at least one second location while maintaining said second tension, such as to induce said second support pressure to said second breast area.

25. A body support for selectively encircling a body part in abutment therewith and supporting at least a first body area and a second body area thereof in a donned configuration, each one of the first body area and the second body area being on a different lateral side of a median plane of the body part, the body support further having a doffed configuration with respect to the body portion, the body support comprising:
a resilient first support panel for abutting the first body area;
a resilient second support panel for abutting the second body area;
a flexible connecting section, joining said first support panel to said second support panel in longitudinal spaced relationship along an imaginary longitudinal mid-line of the body support;
at least one flexible first tongue projecting outwardly from the first support panel in a general first longitudinal direction away from the connecting section, each said first tongue being transversely spaced from said imaginary longitudinal mid-line on a first transverse side of said imaginary longitudinal mid-line;
at least one flexible second tongue projecting outwardly from the second support panel in a general second longitudinal direction away from the connecting section, each said second tongue being transversely spaced from said imaginary longitudinal mid-line on a second transverse side of said imaginary longitudinal mid-line;
said first transverse side and said second transverse side being opposite transverse sides of said imaginary longitudinal mid-line;
a first fastener operative for selectively and reversibly affixing each said first tongue to said second support panel at least at one first relative spatial disposition on said first transverse side of said imaginary longitudinal mid-line; and
a second fastener operative for selectively and reversibly affixing each said second tongue to said first support panel at least at one second relative spatial disposition on said second transverse side of said imaginary longitudinal mid-line,
wherein in the doffed configuration the first support panel and the second support panel are non-contiguous with respect to one another;
and further including at least one of:
(a) wherein the first support panel further comprises at least one first auxiliary tongue projecting from the first support panel in a direction opposite from the at least one flexible first tongue and comprising a first auxiliary fastener configured for selectively and reversibly affixing a respective said at least one first auxiliary tongue with respect to said first support panel at least at one first location, in the donned configuration, such that a portion of said at least one first auxiliary tongue is in overlapping abutting relationship with a respective portion of said first support panel; and
(b) wherein the second support panel further comprises at least one second auxiliary tongue projecting from the second support panel in a direction opposite from the at least one flexible second tongue end and comprising a second auxiliary fastener configured for selectively and reversibly affixing a respective said at least one second auxiliary tongue with respect to said second support panel at least at one second location, in the donned configuration, such that a portion of said at least one second auxiliary tongue is in overlapping abutting relationship with a respective portion of said second support panel.

26. A method of donning a body support on a body portion, comprising:
providing the body support as defined in claim 25;
encircling the torso with the body support such that wherein the first support panel is a first breast receiving panel and is in overlying abutting relationship with a first breast area, the wherein the second support panel is a second breast receiving panel and is in overlying abutting relationship with a second breast area, and the connecting section is in overlying abutting relationship with a back of the torso;

applying a first tension to the first breast receiving panel via a first outer lateral end, and affixing the first breast receiving panel with respect to the second support at a corresponding first position while maintaining said first tension, such as to induce a first support pressure to said first breast area; and applying a second tension to the second breast receiving panel via a second lateral outer end, and affixing the second breast receiving panel with respect to the first support at a corresponding second position while maintaining said second tension, such as to induce a second support pressure to said second breast area.

27. A body support for covering and supporting at least a first body area and a second body area of a body portion, each one of the first body area and the second body area being on a different lateral side of a median plane of the body portion, the body support having a donned configuration and a doffed configuration with respect to the body portion, the body support comprising:

a first support comprising a resilient first panel, a first inner lateral end and a first outer lateral end, wherein said first outer lateral end is free and spaced from said first inner lateral end;

a second support comprising a resilient second panel, a second inner lateral end and a second outer lateral end, wherein said second outer lateral end is free and spaced from said second inner lateral end;

a connecting section joined to the first inner lateral end and to the second inner lateral end for thereby enabling, in the donned configuration, encircling and supporting the body portion when affixed thereto;

at least one first tongue outwardly projecting from said first outer lateral end and comprising a first fastener configured for selectively and reversibly affixing said first support with respect to said second support at least at one first location, in the donned configuration, such that a portion of said at least one first tongue is in overlapping abutting relationship with a respective portion of said second support, wherein to enable a first support pressure to be induced to the first body area by abutting contact therewith; and at least one second tongue outwardly projecting from said second outer lateral end and comprising a second fastener, different from said first fastener, configured for selectively and reversibly affixing said second support with respect to said first support at least at one second location, in the donned configuration, such that a portion of said at least one second tongue is in overlapping abutting relationship with a respective portion of said first support, wherein to enable a second support pressure to be induced to the second body area by abutting contact therewith;

wherein in the doffed configuration the first support and the second support are non-contiguous with respect to one another, and wherein in the donned configuration, a first edge of said first outer lateral end is in abutment with a second edge of said second outer lateral end at an abutment zone in cross-over configuration, wherein to allow a first portion of said first outer lateral end to overlie a second portion of said second outer lateral end, while concurrently allowing a first portion of said second outer lateral end to overlie a second portion of said first outer lateral end;

and further including at least one of:

(a) wherein the first support further comprises at least one first auxiliary tongue projecting from said first outer lateral end and comprising a first auxiliary fastener configured for selectively and reversibly affixing a respective said at least one first auxiliary tongue with respect to said first support at least at another first location, in the donned configuration, such that a portion of said at least one first auxiliary tongue is in overlapping abutting relationship with a respective portion of said first support, wherein to enhance said first support pressure; and (b) wherein the second support further comprises at least one second auxiliary tongue projecting from said second outer lateral end and comprising a second auxiliary fastener configured for selectively and reversibly affixing a respective said at least one second auxiliary tongue with respect to said second support at least at another second location, in the donned configuration, such that a portion of said at least one second auxiliary tongue is in overlapping abutting relationship with a respective portion of said second support, wherein to enhance said second support pressure.

* * * * *